(12) United States Patent
Ruane

(10) Patent No.: US 10,328,247 B2
(45) Date of Patent: *Jun. 25, 2019

(54) POST-PROCESSING OF A MEDICAL DEVICE TO CONTROL MORPHOLOGY AND MECHANICAL PROPERTIES

(71) Applicant: The Spectranetics Corporation, Colorado Springs, CO (US)

(72) Inventor: Patrick H. Ruane, Redwood City, CA (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/949,170

(22) Filed: Apr. 10, 2018

(65) Prior Publication Data

US 2018/0221631 A1 Aug. 9, 2018

Related U.S. Application Data

(63) Continuation of application No. 13/926,515, filed on Jun. 25, 2013, now Pat. No. 9,956,385.

(60) Provisional application No. 61/665,758, filed on Jun. 28, 2012.

(51) Int. Cl.
*A61M 25/10* (2013.01)
*A61L 2/00* (2006.01)
*A61L 29/08* (2006.01)
*A61L 29/16* (2006.01)
*A61L 2/20* (2006.01)
*B05D 3/10* (2006.01)
*B05D 1/18* (2006.01)
*C09D 171/02* (2006.01)

(52) U.S. Cl.
CPC .......... *A61M 25/1029* (2013.01); *A61L 2/00* (2013.01); *A61L 2/206* (2013.01); *A61L 29/085* (2013.01); *A61L 29/16* (2013.01); *B05D 1/18* (2013.01); *B05D 3/107* (2013.01); *C09D 171/02* (2013.01); *A61L 2202/24* (2013.01)

(58) Field of Classification Search
None
See application file for complete search history.

(56) References Cited

U.S. PATENT DOCUMENTS 9,956,385 B2 * 5/2018 Ruane ............... A61M 25/1029
2011/0214785 A1 * 9/2011 Buckman, Jr. ......... B21D 31/00
148/237

* cited by examiner

*Primary Examiner* — Andrew J Bowman

(57) ABSTRACT

A method of forming a coated medical device is described in which a coating including a therapeutic agent dispersed in a polymer or oligomer matrix is applied to an outer surface of the medical device. The coating is then post-processed to selectively remove a substantial portion of the polymer or oligomer matrix from the coating. The post-processed coating is then sterilized.

20 Claims, 12 Drawing Sheets

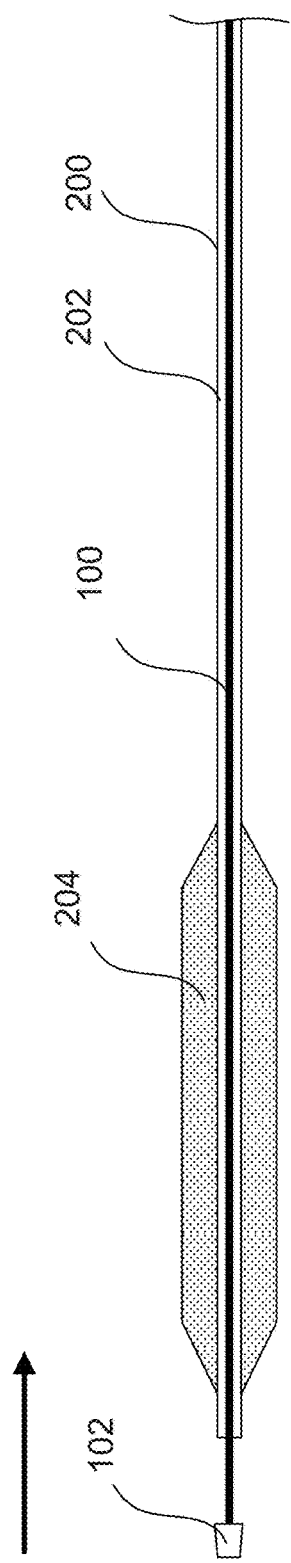
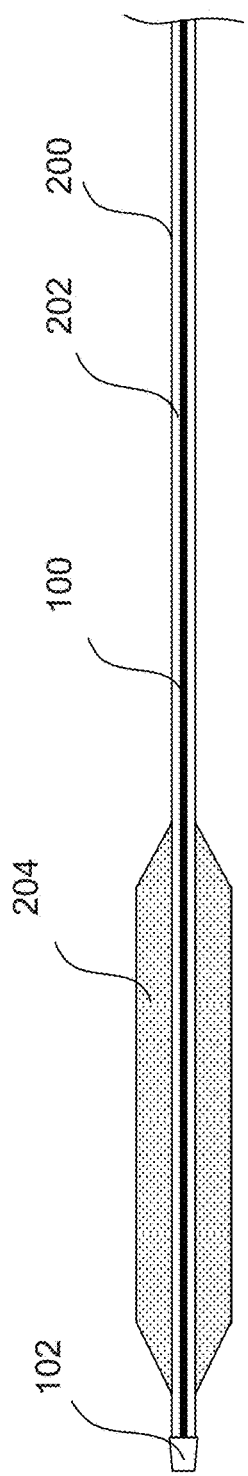
FIG. 1A
FIG. 1B

POST-PROCESSING OF A MEDICAL DEVICE TO CONTROL MORPHOLOGY AND MECHANICAL PROPERTIES

RELATED APPLICATIONS

This application is a continuation of U.S. Application Ser. No.: 13/926,515,filed Jun. 25, 2013, which claims the benefit of and priority to U.S. Provisional Patent Application No. 61/665,758 filed on Jun. 28, 2012, the entire disclosures of each of which are incorporated by reference herein.

FIELD

Embodiments of the present disclosure relate to the field of medical therapeutic agent delivery. More particularly embodiments of the disclosure relate to methods and devices used for local delivery of therapeutic agents to the surface of normal or diseased body lumens.

BACKGROUND

There is a class of medical devices that are insertable into the body with a purpose, wholly or in part, to deliver a therapeutic agent. The intention is either to deliver the therapeutic agent locally at the location of insertion in the body, or to have the therapeutic agent elute systemically. In one implementation of local delivery it may be desired to have rapid delivery of the therapeutic agent to the body tissue, as is the case with some therapeutic agent (drug) coated balloon catheters. In another implementation of local delivery it may be desired to have sustained delivery of the therapeutic agent to the body tissue over a period of weeks or months, as is the case in drug eluting stents.

A polymer or oligomer is often used in the formulation of a coating matrix to contain and control the transfer of the drug into the tissue. In the case of long-term drug release profiles, the polymer can be hydrophobic to prevent dissolution in the aqueous environment of the body, so that the drug releases over time from the matrix via Fickian diffusion. In the case of short term drug release profiles, the polymer may have a hydrophilic character in order to partially dissolve or swell rapidly in the body, so as to help transfer the drug to the tissue upon contact with body fluids in a short period of time on the order of seconds or minutes.

The coating matrix and drug are typically applied to the medical device with a spray application or dip coating process, followed by drying. The coated medical device is then packaged and subjected to a sterilization process to kill any micro organisms which may have been left during production or packaging.

Ethylene oxide (EtO) sterilization is commonly used to sterilize medical and pharmaceutical products that may not be able to withstand high temperatures of a typical autoclave sterilization. A conventional three phase EtO sterilization process is summarized as including a pre-conditioning stage, a sterilizing stage, and an aeration stage. The pre-conditioning stage provides temperature and humidity conditions to incentivize micro organisms to come out of hibernation. The sterilization stage exposes the medical device to EtO gas at a specified temperature and pressure in order to kill the micro organisms. The aeration stage removes the EtO gas and allows the EtO gas to be desorbed.

BRIEF DESCRIPTION OF THE DRAWINGS

FIGS. 1A-1B are cross-sectional side view illustrations of a mandrel being inserted into a guidewire lumen of a balloon catheter in accordance with an embodiment of the disclosure.

DETAILED DESCRIPTION

Figure 2:
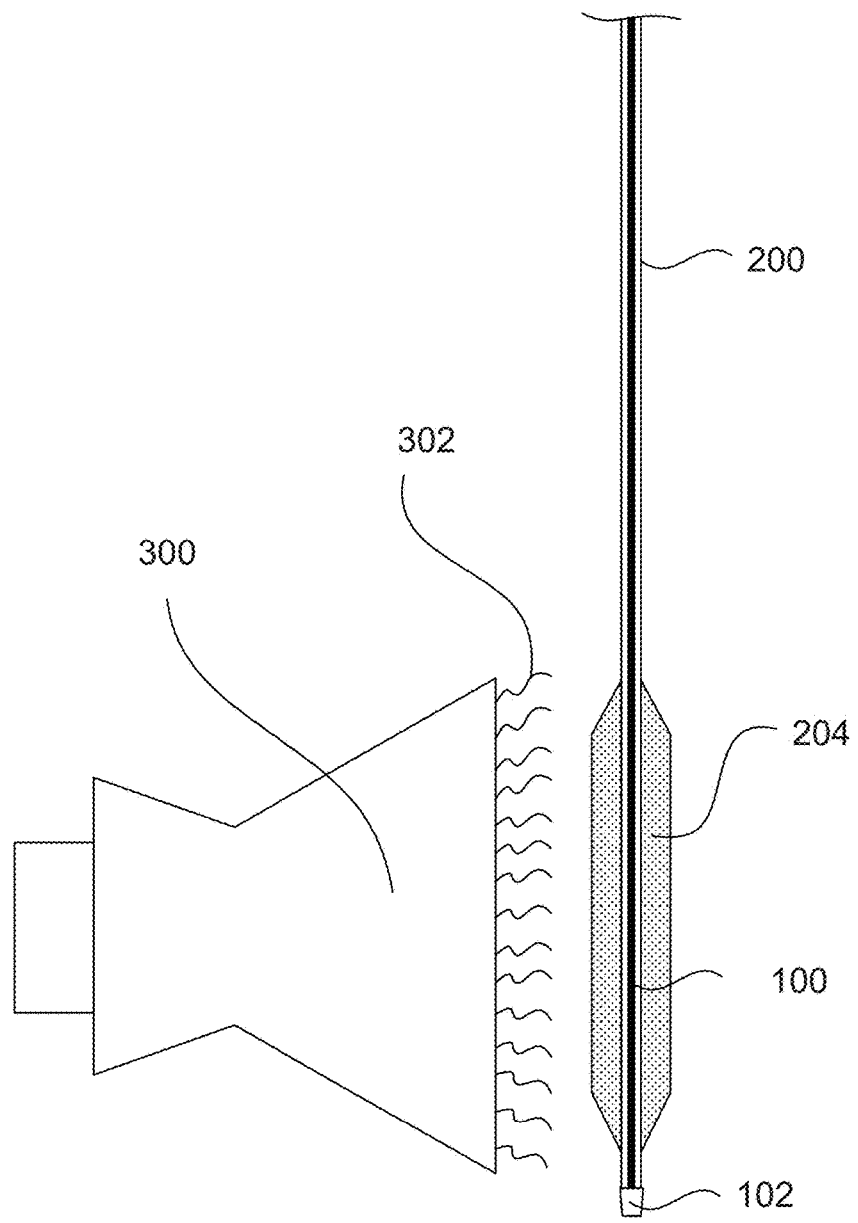
FIG. 2 is a cross-sectional side view illustration of plasma pre-treating a balloon catheter in accordance with an embodiment of the disclosure.

Embodiments of the present disclosure disclose a method of forming a coated medical device in which a coating is applied to an outer surface of the medical device, and post-processed to selectively remove a substantial portion of excipient (e.g. polymer or oligomer matrix) from the coating relative to a therapeutic agent dispersed within the coating. In this manner, a therapeutic agent, excipient, and solvent system with a desired selectivity to the excipient are selected in order to accurately and reproducibly tune a desired loading of therapeutic agent on the medical device while maintaining suitable mechanical characteristics so that functionality of the coating is not lost during clinical use.

Various embodiments are described herein with reference to figures. However, certain embodiments may be practiced without one or more of these specific details, or in combination with other known methods and configurations. In the following description, numerous specific details are set forth, such as specific configurations, compositions, and processes, etc., in order to provide a thorough understanding of the present disclosure. In other instances, well-known processes and manufacturing techniques have not been described in particular detail in order to not unnecessarily obscure the present disclosure. Reference throughout this specification to "one embodiment" or "an embodiment" means that a particular feature, configuration, composition, or characteristic described in connection with the embodiment is included in at least one embodiment of the disclosure. Thus, the appearances of the phrase "in one embodiment" or "an embodiment" in various places throughout this specification are not necessarily referring to the same embodiment of the disclosure. Furthermore, the particular features, configurations, compositions, or characteristics may be combined in any suitable manner in one or more embodiments.

In an embodiment, a method of forming a coated medical device includes applying a coating to an outer surface of a medical device. This fresh coating includes a therapeutic agent dispersed in a coating matrix of polymer or oligomer excipient. The fresh coating is then post-processed to selectively remove a substantial portion of the excipient from the coating relative to the therapeutic agent. The medical device including the post-processed coating is then sterilized.

In one aspect, embodiments of the disclosure describe a manner for controlled production of a coating in which a polymer or oligomer excipient is included in a coating solution to load a desired drug dose onto a medical device by dip coating, followed by a selective removal of the polymer or oligomer excipient in a post-processing operation. The resultant post-processed and sterilized coating provides for uniform tissue dosage with a drug density (as used herein, the drug density is upon inflation to Nominal Inflation Pressure (NIP)) of 0.1-10 µg/mm$^2$, or more specifically 0.7-3.0 µg/mm$^2$. In an embodiment, the resultant post-processed and sterilized coating has a drug density of approximately 2.0 µg/mm$^2$±0.2 µg/mm$^2$.

During the coating process the polymer or oligomer excipient may provide the solution viscosity required to form the coating and load the drug into the coating. Wet film build, or coating thickness, is a function of solution viscosity to the 2/3 power. Accordingly, higher solution viscosity provides higher film thickness, which enables a higher drug dose per unit surface area of the medical device. It has been observed that a drug density of greater than about 0.7 µg/mm$^2$ may be required to provide clinical efficacy in applications such as local delivery of a therapeutic agent for the treatment or inhibition of restenosis, and that a coating solution with greater than 30% by weight (and even as high as 80% by weight) of a polymer or oligomer of the non-volatile components (i.e. not including the solvent, and including the drug and excipient) may be required to achieve this drug density above about 0.7 µg/mm$^2$ in the coating.

In an embodiment, post-processing includes immersing the coated medical device in a solution at a predetermined amount of time, temperature, and orientation in order to control selective removal of the coating matrix excipient relative to the therapeutic agent. In accordance with embodiments of the disclosure, the coating matrix excipient is selectively removed by a significantly higher amount than the therapeutic agent (measured in total weight excipient removed during post-processing divided by the total weight therapeutic agent removed during post-processing). In an embodiment, selective removal is at least 5 times the amount (e.g. 5 µg total excipients compared to 1 µg therapeutic agent removed during post-processing). In an embodiment, selective removal is at least 10 times the amount, or more specifically at least 20 times total excipient to therapeutic agent. In an embodiment, selective removal is as high as 40 times.

As the selectivity increases, so does the relative compositional proportion of the therapeutic agent after post-processing. In an embodiment, the dried fresh coating has a therapeutic agent (Drug) to total excipient (E) weight ratio (D/E) from 20% (1/5 ratio) to 100% (1/1 ratio). As used herein the D in the D/E ratio includes all of the drugs (therapeutic agents) in the coating. As used herein the E in the D/E ratio includes all of the excipients such as polymers, oligomers, penetration enhancers, plasticizers, wax, surfactants, and/or drug solubility enhancers integrated into or dispersed within the coating matrix. In an embodiment, a dry fresh coating prior to post-processing includes less than 50% by weight the therapeutic agent, and a dry post-processed coating includes greater than 50% by weight the therapeutic agent. Thus, the amount of therapeutic agent is transformed from a minority amount in the dry fresh coating to a majority amount in the dry post-processed coating. In an embodiment, a dry fresh coating prior to post-processing includes 35% or less by weight therapeutic agent, and a dry post-processed coating includes 65% or more by weight therapeutic agent. In an embodiment, a dry post-processed coating includes 65%-75% by weight therapeutic agent, and 25%-35% excipient.

Furthermore, as the selectivity increases, the amount of therapeutic agent removed during post-processing may decrease. In an embodiment, the post-processed coating has a D/E ratio from 100% (1/1 ratio) to 9900% (99/1 ratio), or more specifically between 100% and 600% (6/1 ratio). In an embodiment, less than 10% by weight of the therapeutic agent contained in the dry fresh coating is removed from the coating during post-processing, while greater than 75% by weight of excipient contained in the dry fresh coating is selectively removed from the coating during post-processing. In an embodiment, less than 15% by weight of the therapeutic agent contained in the dry fresh coating is removed from the coating during post-processing, while greater than 90% by weight of excipient contained in the dry fresh coating is selectively removed from the coating during post-processing.

In an embodiment, the dried fresh coating has a therapeutic agent (drug) density of approximately 0.1-10.0 µg/mm$^2$, or more specifically approximately 0.7-3.0 µg/mm$^2$. In an embodiment, a post-processed and sterilized coating has a drug density of 0.1-10 µg/mm$^2$, or more specifically 0.7-3.0 µg/mm$^2$. In an embodiment, the resultant post-processed and sterilized coating has a drug density of approximately 2.0 µg/mm$^2$±0.2 µg/mm$^2$.

In one aspect, embodiments of the disclosure describe a manner for controlled production of a coating in which a polymer or oligomer excipient with a hydrophilic character is included in a coating solution to load a desired drug dose of a substantially water insoluble drug onto a medical device, followed by a selective removal of the polymer or oligomer excipient in a post-processing operation to preserve the mechanical properties of the coating when subjected to a sterilization procedure. It has been observed that coating integrity can be affected in response to an EtO sterilization cycle including humidity conditions for coatings including a high amount of hydrophilic polymer or oligomer excipient. This poor coating integrity has also been observed to result in ductile failure of the coating when stressed by bending or inflation (e.g. when formed on a balloon), which can lead to loss of coating material in the form of particulates, and hence drug from the coated device compromising dose uniformity and potential efficacy. In addition, if the particulates are generated in vivo while in transit to the treatment location then clinical sequelai such as emboli may result.

Without being limited to a particular theory, it is believed that a hydrophilic polymer or oligomer excipient absorbs moisture at the controlled temperature and humidity conditions of the EtO sterilization cycle resulting expansion of the hydrophilic polymer or oligomer due to moisture uptake. Upon drying following the sterilization process, removal of the absorbed moisture may result in voids or stress concentrations in the coating leading to coating degradation and ductile failure. It is also contemplated that an amount of polymer or oligomer excipient reflow and phase separation of the substantially water insoluble drug from the hydrophilic polymer or oligomer excipient may occur during the controlled temperature and humidity conditions of the EtO sterilization cycle.

In an embodiment, a coating matrix including a hydrophilic polymer or oligomer excipient possessing aqueous solubility is selectively removed in a post-processing operation in which a dry fresh coating is immersed in an aqueous solution in order to reduce or subvert the coating integrity decrease associated with an EtO sterilization cycle at controlled temperature and humidity conditions. The entirety of the hydrophilic polymer or oligomer is not required to be removed however. In an embodiment, the resultant post-processed coating retains a sufficient amount of a hydrophilic polymer or oligomer excipient so that the coating matrix is still capable of retaining the drug density within a hydrophilic medium which can aid in the transfer of the substantially water insoluble therapeutic agent across the boundary layer between the medical device coating and the adjacent body lumen tissue in vivo.

Thus, in accordance with embodiments of the disclosure, a fresh coating composition can be tailored to include a substantially water insoluble therapeutic agent and excipient possessing chemical characteristics such that upon selection of the appropriate solvent system, the excipient is selectively removed to obtain a post-processed coating including a drug density required to provide clinical efficacy and suitable mechanical characteristics so that functionality of the coating is not lost during clinical use. In accordance with embodiments of the disclosure, a coating process including post-processing and sterilization has been demonstrated that repeatedly produces coatings with good mechanical properties with little to no flaking, and with good coating uniformity across the device surface at accurate drug densities of 0.1-10 $\mu g/mm^2 \pm 10\%$ nominal value, or more specifically 0.7-3.0 $\mu g/mm^2 \pm 10\%$ nominal value. In an embodiment, the resultant post-processed and sterilized coating has a drug density of approximately 2.0 $\mu g/mm^2 \pm 0.2 \mu g/mm^2$.

In the particular embodiments and Examples described in the following description, coatings including a substantially water insoluble therapeutic agent and a polymer or oligomer excipient possessing aqueous solubility are post-processed by immersion in aqueous solution. It is to be appreciated that embodiments are not so limited, and that in other embodiments post-processing can be performed in non-aqueous solution (such as an organic solvent) or aqueous/solvent blends into order to provide the necessary conditions for selective removal of the coating excipients relative to the substantially water insoluble therapeutic agent. In other embodiments, post-processing is performed on a coating including a water soluble therapeutic agent and substantially water insoluble polymer or oligomer excipient, in which the coating is immersed in a solvent to selectively remove the substantially water insoluble polymer or oligomer excipient. Thus, a variety of systems can be produced in accordance with embodiments of the envision in which a therapeutic agent, excipient, and solvent system with a desired selectivity to the excipient are selected in order to accurately and reproducibly selectively remove the excipient and tune a desired amount of therapeutic agent loading on the medical device.

In an embodiment, the dry fresh coating composition prior to post-processing and sterilization, and the final coating composition after post-processing and sterilization include a substantially water insoluble therapeutic agent and one or more excipients. In an embodiment, the substantially water insoluble therapeutic agent is dispersed in a matrix of a hydrophilic yet solvent soluble polymer or oligomer excipient. In an embodiment, a solvent soluble polymer means that the solvent or solvent blend is at least 80% organic solvent by weight, and may be up to 20% by weight water. Optional additional excipients may be penetration enhancers, plasticizers, wax, surfactants, and/or drug solubility enhancers. In an embodiment, the drug solubility enhancer is iodine, that when in the coating associates with the polymer or oligomer, and provides for enhanced solubility of the substantially water insoluble therapeutic agent in aqueous based biological media as described in U.S. Pat. No. 8,128,951. The iodine may be non-covalently bound to the polymer or oligomer. For example, the iodine can be complexed with the polymer or oligomer.

In an embodiment, suitable polymers and oligomers which may be incorporated into the coating composition of the present disclosure include those which are hydrophilic yet solvent soluble including, but not limited to, polyethylene glycol (PEG), polyvinyl pyrrolidone (PVP), hydroxypropyl cellulose (HPC), methyl cellulose, hydroxypropyl methylcellulose, or co-polymers of N-vinylpyrrolidone with other reactive double bond containing monomers such as styrene, acrylic acid, vinyl acetate or vinyl coprolactam. In certain embodiments, the polymer may have a molecular weight below 20,000 Daltons to allow clearance by the kidneys.

In an embodiment, the freshly dried coating comprises approximately 71% by weight PEG 8000 Daltons and approximately 29% by weight paclitaxel, and the fresh coating has a drug density of 0.1-10 $\mu g/mm^2$, and more specifically approximately 2-2.26 $\mu g/mm^2$. In an embodiment, the freshly dried coating comprises approximately 68% by weight PEG 8000 Daltons, approximately 29% by weight paclitaxel, and approximately 3% by weight iodine, and the fresh coating has a drug density of 0.1-10 $\mu g/mm^2$, and more specifically approximately 2-2.26 $\mu g/mm^2$.

In an embodiment, suitable polymers and oligomer excipients which may be incorporated into the coating composition of the present disclosure include bio-erodable polymers such as polylactic acid (PLA), polyglycolic acid (PGA), PLGA, polycaprolactone (PCL) and its copolymers, polyanhydrides, poly(hydroxybutyrate), poly(hydroxybutyrate-co-valerate), polydioxanone, poly(glycolic acid-co-trimethylene carbonate), poly(amino acids), poly(trimethylene carbonate), poly(iminocarbonate), copoly(ether-esters) (e.g., PEO/PLA), polyalkylene oxalates, polyphosphazenes, poly(orthoesters), and polyester-amides.

In an embodiment, suitable bio-polymers (which generally include some hydrophilic character) include fibrin, fibrinogen, hyaluronic acid, chitin, chitosan, alginate, sulfated polysaccharides such as the glycosaminoglycans chondroitin 4-sulfate, chondroitin 6-sulfate, dermatan sulfate, keratan sulfate, heparin, heparan sulfate. Other examples are syndecan, glypican, starch, zein, collagen, gelatin, glycogen, and keratins. Suitable bio-polymers may also include derivatives of cellulose such as methyl cellulose, hydroxypropyl cellulose (HPC), hydroxypropyl methyl cellulose (HPMC), carboxy methyl cellulose (CMC), and ethyl cellulose.

In an embodiment, synthetic non-degradable polymers may be used, some of which may be hydrophilic or hydrophobic depending on specific monomer composition such as acrylate polymer/copolymers, acrylate carboxyl and/or hydroxyl and/or ester copolymers. For example, polyacrylic acid and poly(HEMA) are hydrophilic, whereas poly n-butyl methacrylate (PBMA) is hydrophobic. Block copolymers composed of PEG-PET or PEG-PBT are also suitable; the higher the PEG content, the more hydrophilic the copolymer. In an embodiment, suitable hydrophilic polymers include polyvinylpyrrolidone (PVP), polyvinylpyrrolidone/vinylacetate copolymer (PVPNA), polyethylene glycol, polyethylene oxide, PVA (polyvinyl alcohol), and polyvinylpyridine copolymers. In an embodiment, suitable hydrophobic polymers include olefin acrylic acid copolymer, ethylene acrylic acid copolymer, polyamide polymers/copolymers, polyimide polymers/copolymers, ethylene vinylacetate copolymer, ethylene vinyl alcohol copolymer (EVAL), polysulfones, polyether sulfones, polyurethanes (for example, sold under the registered trademark PELLETHANE, and sold under the registered trademark TECOFLEX), polycarbonate, polyesters, polyethylene terephthalate (PET), polybutylene terephthalate (PBT), block copolymers composed of PEG-PET or PEG-PBT. Additional hydrophobic synthetic non-degradable polymers include polyvinyl chloride and its copolymers, PVAc (polyvinylacetate), styrene-ethylene/butylene-styrene block copolymers (Kraton G, for example, sold under the registered trademark KRATON), styrene-polydiene-styrene block copolymers (Kraton D, for example, sold under the registered trademark KRATON). Additional hydrophobic synthetic non-degradable polymers include polyvinylidene fluoride and its copolymers (for example, sold under the trademeark KYNAR, and sold under the registered trademark SOLEF).

In one aspect, embodiments of the disclosure disclose a substantially water insoluble therapeutic agent to treat a variety of diseases that arise in body lumen walls. The therapeutic agents useful in accordance with the present disclosure may be used singly or in combination. Certain embodiments of the disclosure related to method of coating a composition comprising a taxane therapeutic agent, such as paclitaxel, onto a medical device. Taxanes in general, and paclitaxel in particular, are taxane therapeutic compounds considered to function as a cell cycle inhibitors by acting as an anti-microtubule agent, and more specifically as a stabilizer. As used herein, the term "paclitaxel" refers to a compound of the chemical structure shown as structure (1) below,

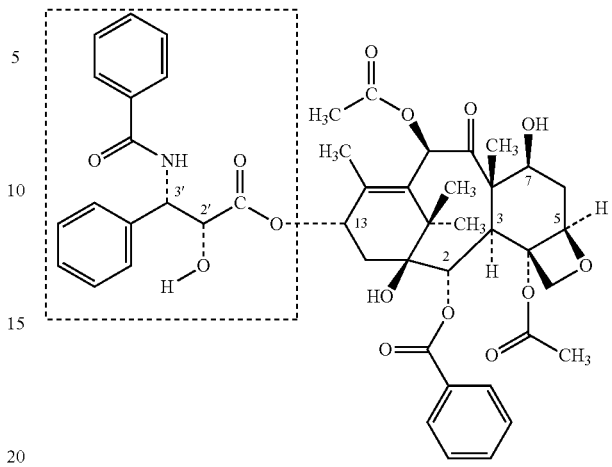

(1)

consisting of a core structure with four fused rings ("core taxane structure," shaded in structure (1)), with several substituents.

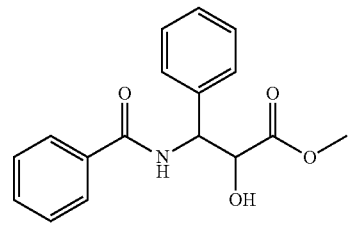

(2)

methyl 3-(benzamido)-2-hydroxy-3-phenylpropanoate

Other taxane analog or derivative compounds are characterized by variation of the paclitaxel structure (1). Preferred taxane analogs and core derivatives vary the substituents attached to the core taxane structure. In one embodiment, the therapeutic agent is a taxane analog or derivative including the core taxane structure (1) and the methyl 3-(benzamido)-2-hydroxy-3-phenylpropanoate moiety (shown in structure (2) below) at the 13-carbon position ("C13") of the core taxane structure (outlined with a dashed line in structure (1)).

It is believed that structure (2) at the 13-carbon position of the core taxane structure plays a role in the biological activity of the molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-nitrophenyl)-N-debenzoyl-N-(t-butoxycarbonyl)-10-deacetyltaxol.

Representative examples of paclitaxel derivatives or analogues that can be used as therapeutic agents include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG (5000) carbamate taxol, 2'-benzoyl and 2',7-dibenzoyl taxol derivatives, other prodrugs (2'-acetyltaxol; 2',7-diacetyltaxol; 2'-succinyltaxol; 2'-(beta-alanyl)-taxol); 2'-gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino)propionyl)taxol; 2'-orthocarboxybenzoyl taxol; 2'-aliphatic carboxylic acid derivatives of taxol, Prodrugs {2'-(N,N-diethylaminopropionyl)taxol, 2'-(N,N-dimethylglycyl)taxol, 7-(N,N-dimethylglycyl)taxol, 2',7-di-(N,N-dimethylglycyl) taxol, 7-(N,N-diethylaminopropionyl)taxol, 2',7-di(N,N-diethylaminopropionyl)taxol, 2'-(L-glycyl)taxol, 7-(L-glycyl) taxol, 2',7-di(L-glycyl)taxol, 2'-(L-alanyl)taxol, 7-(L-alanyl) taxol, 2',7-di(L-alanyl)taxol, 2'-(L-leucyl)taxol, 7-(L-leucyl) taxol, 2',7-di(L-leucyl)taxol, 2'-(L-isoleucyl)taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl) taxol, 7-(L-phenylalanyl)taxol, 2',7-di(L-phenylalanyl) taxol, 2'-(L-prolyl)taxol, 7-(L-prolyl)taxol, 2',7-di(L-prolyl) taxol, 2'-(L-lysyl)taxol, 7-(L-lysyl)taxol, 2',7-di(L-lysyl) taxol, 2'-(L-glutamyl)taxol, 7-(L-glutamyl)taxol, 2',7-di(L-glutamyl)taxol, 2'-(L-arginyl)taxol, 7-(L-arginyl)taxol, 2',7-di(L-arginyl)taxol}, taxol analogues with modified phenylisoserine side chains, (N-debenzoyl-N-tert-(butoxycarbonyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, dibenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, sulfonamide taxane derivatives, brominated paclitaxel analogues, Girard taxane derivatives, nitrophenyl paclitaxel, 10-deacetylated substituted paclitaxel derivatives, 14-beta-hydroxy-10 deacetylbaccatin III taxane derivatives, C7 taxane derivatives, C10 taxane derivatives, 2-debenzoyl-2-acyl taxane derivatives, 2-dibenzoyl and -2-acyl paclitaxel derivatives, taxane and baccatin III analogues bearing new C2 and C4 functional groups, n-acyl paclitaxel analogues, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, ortho-ester paclitaxel analogues, 2-aroyl-4-acyl paclitaxel analogues and 1-deoxy paclitaxel and 1-deoxy paclitaxel analogues.

A composition comprising a taxane compound can include formulations, prodrugs, analogues and derivatives of paclitaxel such as, for example, TAXOL (Bristol Myers Squibb, New York, N.Y.), docetaxel, 10-desacetyl analogues of paclitaxel and 3'-N-desbenzoyl-3'-N-t-butoxy carbonyl analogues of paclitaxel. Paclitaxel has a molecular weight of about 853 amu, and may be readily prepared utilizing techniques known to those skilled in the art (see, e.g., Schiff et al., Nature 277: 665-667, 1979; Long and Fairchild, Cancer Research 54: 4355-4361, 1994; Ringel and Horwitz, J. Nat'l Cancer Inst. 83 (4): 288-291, 1991; Pazdur et al., Cancer Treat. Rev. 19 (4): 351-386, 1993; WO 94/07882; WO 94/07881; WO 94/07880; WO 94/07876; WO 93/23555; WO 93/10076; W094/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; Tetrahedron Letters 35 (52): 9709-9712, 1994; J. Med. Chem. 35: 4230-4237, 1992; J. Med. Chem. 34: 992-998, 1991; and J. Natural Prod. 57 (10): 1404-1410, 1994; J. Natural Prod. 57 (11): 1580-1583, 1994; J. Am. Chem. Soc. 110: 6558-6560, 1988), or obtained from a variety of commercial sources, including for example, Sigma Chemical Co., St. Louis, Mo. (T7402—from *Taxus brevifolia*).

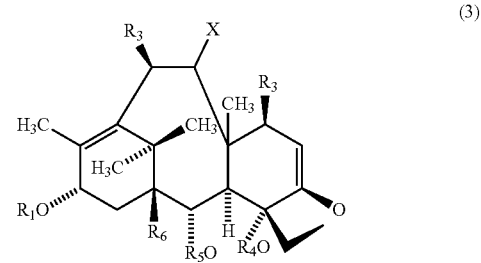

(3)

In one aspect, the therapeutic agent is selected from the taxane analogues and derivatives disclosed in U.S. Pat. No. 5,440,056 as having the structure (3):
wherein X may be oxygen (paclitaxel), hydrogen (9-deoxy derivatives), thioacyl, or dihydroxyl precursors; $R_1$ is selected from paclitaxel or TAXOTERE side chains or alkanoyl of the formula (4):

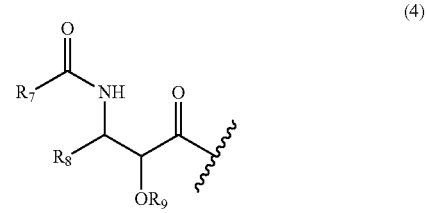

(4)

wherein $R_7$ is selected from hydrogen, alkyl, phenyl, alkoxy, amino, phenoxy (substituted or unsubstituted); $R_8$ is selected from hydrogen, alkyl, hydroxyalkyl, alkoxyalkyl, aminoalkyl, phenyl (substituted or unsubstituted), alpha or beta-naphthyl; and $R_9$ is selected from hydrogen, alkanoyl, substituted alkanoyl, and aminoalkanoyl; where substitutions refer to hydroxyl, sulfhydryl, alkoxyl, carboxyl, halogen, thioalkoxyl, N,N-dimethylamino, alkylamino, dialkylamino, nitro, and sulfate(—$OSO_3H$), and/or may refer to groups containing such substitutions; $R_2$ is selected from hydrogen or oxygen-containing groups, such as hydrogen, hydroxyl, alkoxyl, alkanoyloxy, aminoalkanoyloxy, and peptidyalkanoyloxy; $R_3$ is selected from hydrogen or oxygen-containing groups, such as hydrogen, hydroxyl, alkoxyl, alkanoyloxy, aminoalkanoyloxy, and peptidyalkanoyloxy, and may further be a silyl containing group or a sulphur containing group; $R_4$ is selected from acyl, alkyl, alkanoyl, aminoalkanoyl, peptidylalkanoyl and aroyl; $R_5$ is selected from acyl, alkyl, alkanoyl, aminoalkanoyl, peptidylalkanoyl and aroyl; $R_6$ is selected from hydrogen or oxygen-containing groups, such as hydrogen, hydroxyl alkoxyl, alkanoyloxy, aminoalkanoyloxy, and peptidyalkanoyloxy.

In one aspect, the therapeutic agent is selected from the paclitaxel analogues and derivatives disclosed in PCT International Patent Application No. WO 93/10076 as cell cycle inhibitors. The analogue or derivative may have a side chain attached to the taxane nucleus at C13, as shown in the structure below (formula 5), in order to confer antitumor activity to the taxane.

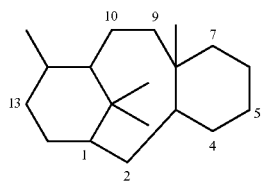

(5)

WO 93/10076 discloses that the taxane nucleus may be substituted at any position with the exception of the existing methyl groups. The substitutions may include, for example, hydrogen, alkanoyloxy, alkenoyloxy, aryloyloxy. In addition, oxo groups may be attached to carbons labeled 2, 4, 9, and/or 10. As well, an oxetane ring may be attached at carbons 4 and 5. As well, an oxirane ring may be attached to the carbon labeled 4. In one aspect, the taxane-based cell cycle inhibitor useful in the present disclosure is disclosed in U.S. Pat. No. 5,440,056, which discloses 9-deoxo taxanes. These are compounds lacking an oxo group at the carbon labeled 9 in the taxane structure shown above in formula (5). The taxane ring may also be substituted at the carbons labeled 1, 7 and 10 (independently) with H, OH, O—R, or O—CO—R where R is an alkyl or an aminoalkyl. As well, it may be substituted at carbons labeled 2 and 4 (independently) with aroyl, alkanoyl, aminoalkanoyl or alkyl groups. The side chain of formula (4) may be substituted at $R_7$ and $R_8$ (independently) with phenyl rings, substituted phenyl rings, linear alkanes/alkenes, and groups containing H, O or N. $R_9$ may be substituted with H, or a substituted or unsubstituted alkanoyl group.

In an embodiment, a non-aqueous soluble anti-proliferative agent such as paclitaxel may be used in combination with another therapeutic agent such as the anti-inflammatory agent dexamethasone. In an embodiment, therapeutic agents which may be, singly or in combination, locally delivered to the surface of normal or diseased body lumens can be classified into the categories of anti-proliferative agents, anti-platelet agents, anti-inflammatory agents, anti-thrombotic agents, and thrombolytic agents. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of non-aqueous soluble vinca alkaloids include, but are not limited to, paclitaxel (including the alkaloid itself and naturally occurring forms and derivatives thereof, as well as synthetic and semi-synthetic forms thereof), vincristine, etoposide, indirubin, and anthracycline derivatives, such as, for example, daunorubicin, daunomycin, and plicamycin. Other sub-classes of anti-mitotic agents include anti-mitotic alkylating agents, such as, for example non-aqueous soluble fotemustine, and anti-mitotic metabolites, such as, for example, non-aqueous soluble azathioprine, mycophenolic acid, leflunomide, teriflunomide, fluorouracil, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Examples of non-aqueous soluble anti-inflammatory agents that can also be used include, but are not limited to, dexamethasone, prednisone, hydrocortisone, estradiol, triamcinolone, mometasone, fluticasone, clobetasol, and non-steroidal anti-inflammatories, such as, for example, acetaminophen, ibuprofen, and sulindac. The arachidonate metabolite prostacyclin or prostacyclin analogs are examples of a vasoactive antiproliferative.

Therapeutic agents with pleiotropic effects on cell proliferation, immunomodulation and inflammation may also be used. Examples of such non-aqueous soluble agents include, but are not limited to the macrolides and derivatives thereof such as sirolimus (e.g. rapamycin), tacrolimus, everolimus, temsirolimus.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Non-aqueous soluble anti-platelet agents that act as inhibitors of adhesion of platelets include, but are not limited to, and tirofiban and RGD (Arg-Gly-Asp)-based peptides (Pegylated) that inhibit binding to gpIIbIIIa or αv.β3, compounds that block P-selectin or E-selectin binding to their respective ligands. Agents that inhibit ADP-mediated platelet aggregation include, but are not limited to, cilostazol.

Anti-thrombotic agents include chemical and biological entities that can intervene at any stage in the coagulation pathway. Examples of specific non-aqueous soluble entities include, but are not limited to, small molecules that inhibit the activity of factor Xa. Also included are direct thrombin inhibitors, such as, for example, argatroban, inogatran.

Other non-aqueous soluble therapeutic agents that can be used are cytotoxic drugs, such as, for example, apoptosis inducers, and topoisomerase inhibitors, including, irinotecan, and doxorubicin, and drugs that modulate cell differentiation such as inhibitors of histone deacetylase, including valproic acid.

Other non-aqueous soluble therapeutic agents that can be used include anti-lipaedemic agents, including but not limited to fenofibrate, clofibrate, and rosiglitazone and matrix metalloproteinase inhibitors, such as, for example, batimistat, antagonists of the endothelin-A receptor, such as, for example, darusentan.

In another embodiment, aqueous soluble therapeutic agents may be used. Aqueous soluble anti-mitotic agents include Epothilone A, Epothilone B and Epothilone D, and all other Epothilones. Aqueous soluble anti-platelet agents include RGD (Arg-Gly-Asp)-based peptides that inhibit binding to gpIIbIIIa or αv.β3. Aqueous soluble anti-thrombotic agents include heparinoid-type agents that can inhibit both FXa and thrombin, either directly or indirectly, such as heparin, heparin sulfate, low molecular weight heparins such as the compound having the registered trademark CLIVARIN, and synthetic oligosaccharides such as the compound having the registered trademark ARIXTRA. Aqueous soluble thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase. Additional aqueous soluble therapeutic agents include recombinant antibodies for anti-platelet and anti-endothelin applications.

Coating Solution Preparation

In an embodiment, a coating solution includes a therapeutic agent, one or more excipients, and a solvent. The coating solution is formulated with sufficient polymer or oligomer excipient, in the case of dip coating, to provide a useful viscosity to achieve the desired drug concentration on the device. In an embodiment, the coating solution viscosity is between 5 centipoise (cps) and 75 cps, or more specifically between 20 cps and 30 cps. This may require the polymer or oligomer excipient portion to account for greater than 30% and as much as 80% by weight of the non-volatile matter in the coating solution.

In an embodiment, the required amount of polymer or oligomer excipient and drug are weighed and added to a suitable mixing container such as a volumetric flask. A requisite amount of solvent is then added to the mixing container. In an embodiment, the solvent is a mixture of ethanol/acetonitrile. In an embodiment, the solvent is a 57/43 azeotrope solution (by mass) of ethanol/acetonitrile. The coating solution components may then be vortexed under heat to dissolve the polymer excipient and drug in the solvent. Where an additional excipient such as iodine is included, a requisite amount of molecular iodine may then be weighed and added to the solution and dissolved under heat and vortex. In an embodiment, the coating solution includes, by weight % non-volatiles, approximately 30-95% excipient and 5-70% drug, or more specifically approximately 60-80% excipient and 20-40% drug. In an embodiment, the coating solution includes, by weight % non-volatiles, approximately 68% PEG excipient, approximately 29% paclitaxel, and approximately 3% molecular iodine excipient. Where the polymer excipient comprises PEG the dissolving operations under heat and vortex may be performed at approximately 42° C.±2° C. in accordance with an embodiment.

In an embodiment, a majority or exclusively non-aqueous solvents in the coating solution provides rapid evaporation, a lower surface tension, and improved substrate wetting compared to an aqueous solution, which aids in coating uniformity. In an embodiment, a suitable solution may contain a solvent or solvent blend which is at least 80% organic solvent by weight, and may be up to 20% by weight water. For example, solvents with boiling points lower than water can be used singly or in combination in the coating solution, such as ethanol, methanol, methyl ethyl ketone, isopropanol (2-propanol), and acetonitrile. In one embodiment, the use of a minor solvent component with a boiling point greater than water, such as n-butanol, may be used.

Balloon Pre-conditioning

Initially, the balloon catheter is removed from its packaging, including the protective sheath covering the balloon. The balloon catheter is then hung on a catheter tree such that the balloon is pointing downward towards the ground. The balloon is then inflated by injecting a gas through the balloon port. In an embodiment, the balloon is inflated just to the point of removing any folds of the balloon.

In some embodiments, the inflated balloon may then be sonicated in 99% isopropyl alcohol (IPA) using a cascade wash process in order to clean the surface of the balloon. The washing process may be repeated 1 to 10 times, and may last from 60 seconds±5 seconds to 15 seconds±5 seconds. The balloon may then dried by blowing filtered air over the surface of the balloon and through the guidewire lumen.

Referring now to FIGS. 1A-1B, a capped and appropriately sized mandrel 100 is inserted into the balloon catheter guidewire lumen 202 until the cap 102 is secured against the distal end of the balloon catheter. An exemplary list of appropriately sized mandrels is provided in Table 1 below.

TABLE 1

| Balloon Length | Mandrel Size |
| --- | --- |
| 20 mm | 0.90 mm × 127 mm |
| 40 mm | 0.90 mm × 152 mm |
| 60 mm | 0.90 mm × 178 mm |
| 80 mm | 0.90 mm × 203 mm |
| 120 mm | 0.90 mm × 229 mm |

With the balloon 204 still inflated, the balloon is then optionally plasma pre-treated in order to increase wettability of the balloon surface prior to coating. In accordance with an embodiment illustrated in FIG. 2 an atmospheric plasma generator including a duck bill nozzle 300 is then placed 1 cm±0.5 cm from the edge of the balloon 204. The duck bill nozzle may be centrally aligned so as to encompass the maximum length of the balloon. The balloon is then rotated at a speed of 60 rpm±2 rpm. Gas flow is set to 15 psi, and the plasma intensity set to 80% on the plasma generator and the balloon is pre-treated with plasma 302 for 30 seconds. Power to the plasma generator is then turned off. Suitable treatment gases include air, argon, nitrogen, oxygen, or a mixture of $CF_4$ and oxygen. In an embodiment, the mandrel is formed of a electrically insulating material, such as a ceramic, in order to avoid arcing from the plasma generator.

Coating Process

Figure 3:
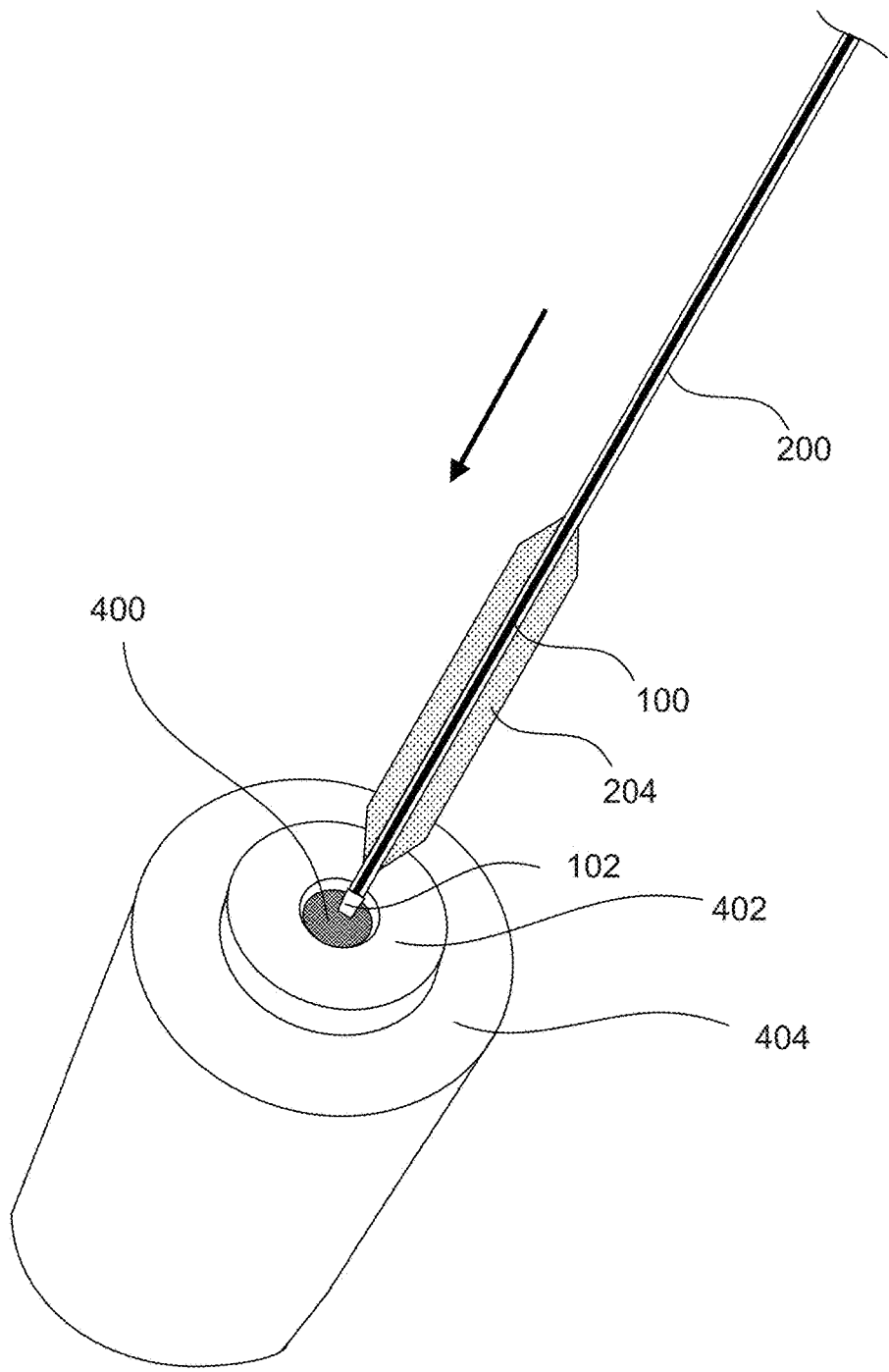
FIGS. 3-4 are combination isometric and cross-sectional view illustrations of dip coating a balloon catheter in accordance with an embodiment of the disclosure.
Figure 4:
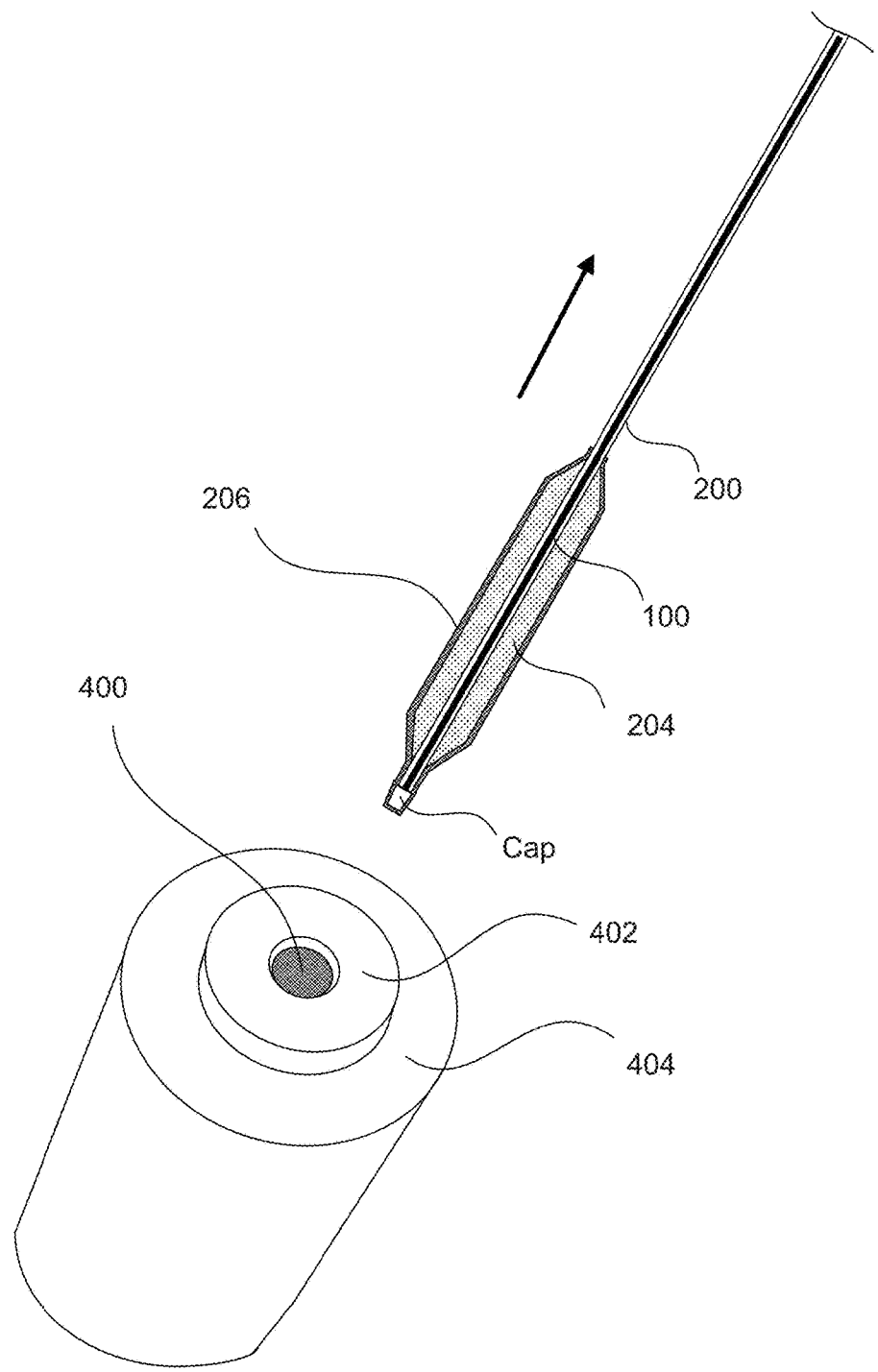

The coating can be formed from a variety of techniques including dip coating, deposition, spray coating, ultrasonic spray coating, and flow coating amongst others. FIGS. 3-4 illustrate an embodiment in which the coating 206 is formed by dip coating a balloon 204 of a balloon catheter into a coating solution 400. Utilizing embodiments of the disclosure, the dip coating process can provide a uniform therapeutic agent density across the balloon surface using a reproducible single-dip, thereby eliminating the need for multiple dips to load the therapeutic agent into the coating. As described in further detail in the following examples, utilizing embodiments of the disclosure, a method of forming a single-dip coating followed by post-processing and sterilization is disclosed which results in uniform process Acceptance Value (AV) calculated in accordance with United States Pharmacopeia's (USP) chapter 905, "Uniformity of Dosage Units." The single-dip process in accordance with embodiments of the disclosure is fast and relieves engineering controls associated with other coating techniques such as spray coating, which may include spraying hazardous materials in a fume hood, and spray inconsistencies associated with nozzle tip variations and drug crystallization variation during spray application.

Prior to coating, a reservoir 402 is filled with the coating solution 400. For example, the reservoir may be formed of polytetrafluoroethylene (PTFE). In an embodiment, a heater jacket 404 is utilized to equilibrate the coating solution at 70° F. (or room temperature) for 5 minutes prior to dip coating the balloon 204. For example, the heater jacket may be formed of aluminum. Temperatures other than room temperature may be selected, with evaporative loss of the solvent (aqueous, non-aqueous, or mixture) being a factor in selecting reservoir temperature, since evaporation of the solvent can cause changes in coating composition uniformity. In an embodiment, a plurality of medical devices can be consecutively dip coated in the same coating solution, with an acceptable AV of the final post-processed and sterilized lot of medical devices. In an embodiment, up to 200 or more medical devices are consecutively dip coated in the same coating solution with an acceptable AV of the final post-processed and sterilized lot of medical devices.

The medical device may be rotated during dip coating, and the rpm can vary from 10 to 100 rpm. The medical device may be oriented at 90 degrees from horizontal or at an angle, for example 45 degrees, or any angle between. Lower angles will impart less gravitational force to the wet coating as it is drying. The extraction speed from the coating solution can vary from 0.01 inches/second to 2 inches per second. Higher extraction speeds may apply more coating to the device. Drug density, in the case of paclitaxel on a drug eluting balloon, can vary from 0.1 µg/mm$^2$ to 10 µg/mm$^2$ on the balloon surface, or more specifically 0.7-3.0 µg/mm$^2$.

In the case of a balloon catheter, the cap 102 on the mandrel is positioned at the meniscus of the coating solution 400 as illustrated in FIG. 3. The balloon 204 is then dipped into the coating solution 400 until the balloon reaches the maximum immersion depth. In an embodiment, the balloon has not been rotating up to this point. Once the maximum immersion depth is reached, the balloon dwells at the immersion depth for a period of time, such as 5 seconds. The balloon is then extracted from the coating solution as illustrated in FIG. 4. In an embodiment, rotation of the balloon is commenced at the beginning or end of the dwell time, and the balloon continues to rotate during extraction from the coating solution. In an embodiment, the balloon does not rotate during the dwell time or extraction.

Upon extraction from the coating reservoir, the coated device may be rotated at the coating angle until sufficient solvent has evaporated to raise the coating viscosity to the point at which the coating 206 is "set" and will resist sagging if moved from this location. This time may be from 10 seconds to 10 minutes. After the coating 206 is applied and "set" the cap 102 and mandrel 100 are removed from the balloon catheter and the remaining solvents are removed by storing in ambient conditions or controlled temperature and air velocity conditions, or in a vacuum or vacuum oven until the residual solvents are below 1% of the coating 206 by weight. The full dry time can be as long as 24 hours or longer. As described in the following description, coating 206 is referred to as a "fresh" coating prior to post-processing and sterilization.

Post-processing

In an embodiment, post-processing may be performed after the "fresh" coating is "set" or after the fresh coating is fully dried. Prior to post-processing a ceramic or stainless steel mandrel is inserted into the guidewire lumen, and the balloon with a dried fresh coating is gently inflated to unfold the balloon. In an embodiment, post-processing involves immersion of the dried fresh coating into a water reservoir at a controlled temperature such as 75° F.±5° F. A PTFE reservoir and heater jacket similar to the dip coating apparatus described in FIGS. 3-4 can be utilized for post-processing water immersion. In an embodiment, the water is a pyrogen-free grade, and is changed out between post-processing of each device.

Similar to the description of FIGS. 3-4, the cap on the mandrel is positioned at the meniscus of the pyrogen-free water. The inflated balloon may be inserted into the water reservoir at an angle, such as 45 degrees from horizontal, vertically, or any angle between. Immersion time can vary from 2 seconds to 5 minutes, and the balloon may be rotated while in the water for any period of time after extraction from the water bath. In an embodiment, the withdrawal rate from the bath is 0.1-2 inches per second, or more specifically between 0.3-1.3 inches per second. In an embodiment, the withdrawal rate from the bath is 0.31 inches per second. Optionally, a filtered air jet may be used to remove water droplets on the device surface after it has been extracted from the water bath. The device may then be dried in ambient conditions or controlled temperature and air velocity conditions, or in a vacuum or vacuum oven, from 1 hour to 24 hours to remove the water.

Sterilization Process

In the case of a balloon catheter, the balloon is folded, sheathed, and packaged following drying of the post-processed coating. A list of appropriately sized flared sheaths is provided in Table 2 below.

TABLE 2

| Balloon size | Sheath measurement | French size |
| --- | --- | --- |
| 3 × 20 mm | 1.68 mm × 55 mm | 5 Fr |
| 4 × 40 mm | 2.01 mm × 75 mm | 6 Fr |
| 5 × 40 mm | 2.01 mm × 75 mm | 6 Fr |
| 6 × 40 mm | 2.01 mm × 75 mm | 6 Fr |
| 6 × 60 mm | 2.01 mm × 90 mm | 6 Fr |
| 5 × 80 mm | 2.01 mm × 115 mm | 6 Fr |
| 6 × 80 mm | 2.01 mm × 115 mm | 6 Fr |
| 7 × 80 mm | 2.33 mm × 115 mm | 7 Fr |

Figure 5:
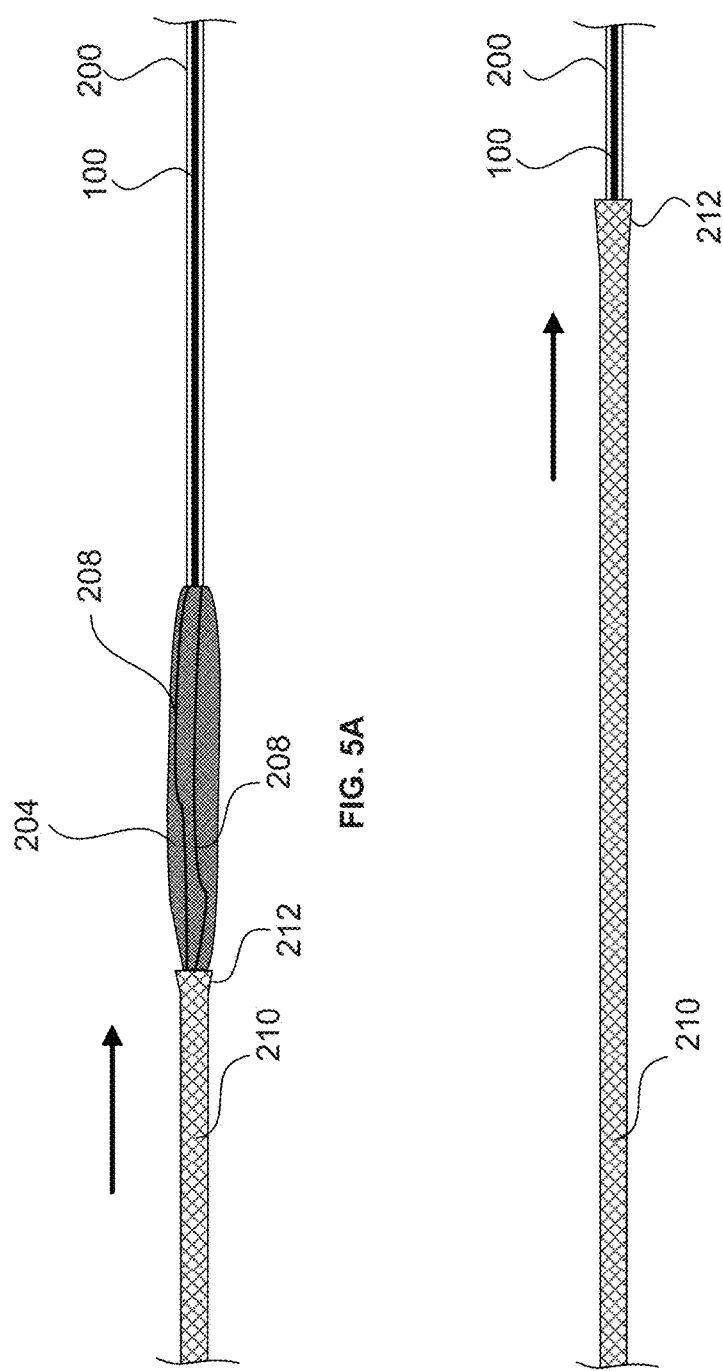
FIGS. 5A-5B are side view illustrations of sheathing a coated balloon in accordance with an embodiment of the disclosure.
Figure 6:
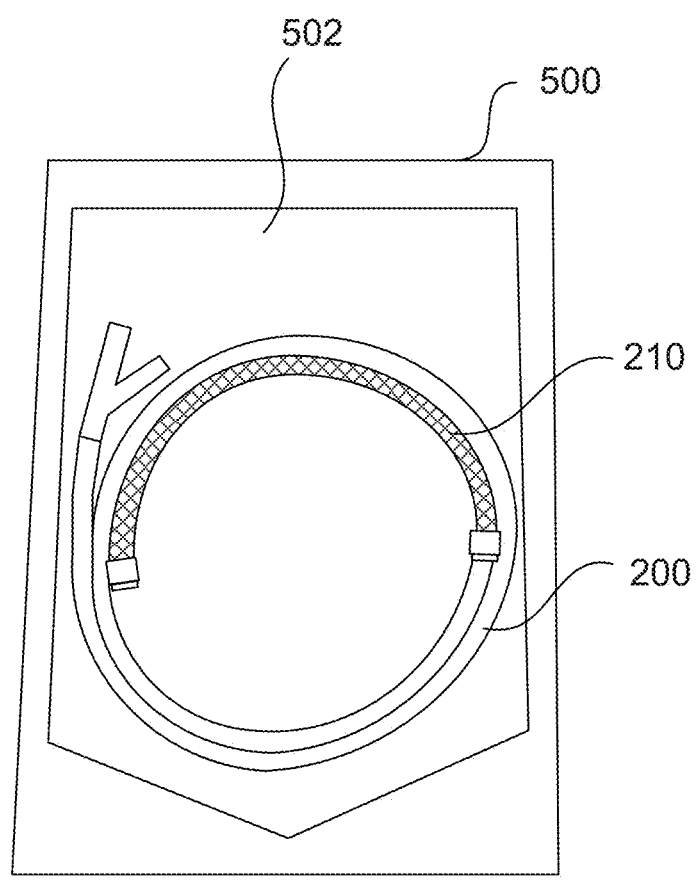
FIG. 6 is a top view illustration of a sheathed balloon catheter in a sterilization package in accordance with an embodiment of the disclosure.

Using a stop-cock and syringe, negative pressure is slowly drawn in the coated balloon to deflate the balloon. Referring now to FIGS. 5A-5B, the balloon 204 is then refolded and smoothed. In an embodiment, the balloon 204 is refolded into its original folded configuration. Additional negative pressure may be drawn to lay folds 208 in the original fold direction, such as a clockwise direction. An appropriately sized flared sheath 210 is loaded onto the mandrel 100 with the flared end 212 first, toward the distal end of the balloon 204. The folded balloon 204 is then inserted into sheath 210 while twisting the sheath in the clockwise direction. Once the sheath 210 is drawn over the balloon 204, the mandrel 100 may be removed. The sheathed balloon catheter may then be inserted into the original packaging hoop, and placed into a suitable sterilization packaging, such as a bag, pouch, tube or mold. FIG. 6 is an illustration of a sheathed balloon catheter 200 within a sealed sterilization package 500. In an embodiment, the sterilization package 500 includes a see-through outer film 502 of flashspun high-density polyethylene fibers (also known as TYVEK(R) which is a registered trademark of DuPont) that allows the moisture and heat from EtO sterilization to pass in and to pass out of the package.

In an embodiment, the sterilization process is a three phase process including a pre-conditioning stage, a sterilizing stage, and an aeration stage. In an embodiment, the pre-conditioning stage includes loading the sterilization package into a chamber maintained at 60% ±5% relative humidity at 41° C.±3° C. for 60 minutes±3 minutes. The sterilization stage is then initiated by puncturing a 100 gram EtO cartridge to admit EtO gas into the chamber which is held at 41° C.±3° C., 99 mBar −10/+20 mBar, for an exposure time of ≥10 hours −0/+1 hours. The chamber is then flushed with air at a pressure of 128 mBar −10/+25 mBar at a temperature of 41° C.±3° C. for an aeration time of 1 hours −0/+12 hours, followed by external aeration for approximately 24 hours at 21° C.±3° C.

EXAMPLE 1

A coating solution was made as follows: to a 10 ml volumetric flask was added 1.45 grams polyethylene glycol (PEG) 8 kDa (Dow Carbowax Sentry), 0.615 grams paclitaxel (Yunnan-Hande) and about 8 mL of a 57/43(by weight) blend of ethanol and acetonitrile. The mixture was alternately warmed in a water bath at 42° C. and vortexed to dissolve the drug and polymer. After the solids were dissolved, 68.0 mg of iodine were added and additional 57/43 ethanol/acetonitrile added to about approximately 0.5 cm below the mark. The mixture was vortexed and heated at 42° C. in the water bath to dissolve the iodine. Finally, an addition of 57/43 ethanol/acetonitrile was made to the volumetric mark once the solution had returned to room temperature. The solution was capped and vortexed.

A balloon catheter (ev3 EVERCROSS™, 5.0×40 mm) was prepared as follows. The balloon was gently inflated with a syringe and pressure was held with a stopcock. The inflated balloon was sonicated in 99% 2-Propanol using a cascade wash process for a total of 3 washes. The first sonication was 60 seconds, the second was 30 seconds and the third was 15 seconds. The balloon was dried with a jet of filtered air applied to the surface and the guidewire lumen. The catheter was mounted onto a fixture that permits rotation of the balloon. The distal end of the catheter was loaded with a ceramic mandrel to aid in straightening the balloon section. The balloon, thus fixtured, was loaded onto an automated dip station that permits controlled-speed angular dipping and rotation. The balloon was rotated at 58 rpm±2 rpm at a distance of 1 cm from a duck bill nozzle of a Tri-star PT2000P atmospheric plasma treater using argon as the treatment gas. Gas flow was set to 15 psi, plasma intensity to 80%, and treatment time was 30 seconds.

The coating solution was then transferred to a temperature controlled jacketed reservoir and equilibrated to 70° F. for 5 minutes while capped. The reservoir was placed on the dip station. The cap was removed and the balloon was dipped fully into the solution (at a 90° angle), held for 5 seconds, then rotated at 58 rpm±2 rpm and extracted from the solution at a speed of 1 inch per second. The balloon was rotated for an additional minute in the atmosphere, then removed from the fixture and hung on a catheter tree to dry for 24 hours. An identical balloon processed as above was tested for drug content, and shown to have a drug surface density of 2.13 µg/mm² of balloon surface.

After 24 hours, a cylindrical polytetrafluoroethylene (PTFE) reservoir was loaded with pyrogen-free water and held at 70° F. The balloon was gently re-inflated and immersed completely into the water for 45 seconds at a 90 degree angle from horizontal. No rotation was used. At the end of 45 seconds the balloon was removed at a rate of 0.315 inches per second then transferred to a catheter tree to dry overnight.

The dried balloon catheter was then sheathed and packaged in a sterilization package. The sterilization package was then pre-treated a chamber maintained at 60%±5% relative humidity at 41° C.±3° C. for 60 minutes±3 minutes, followed by puncturing a 100 gram EtO cartridge to admit EtO gas into the chamber which was held at 41° C.±3° C., 99 mBar −10/+20 mBar, for an exposure time of ≥10 hours −0/+1 hours. The chamber was then flushed with air at a pressure of 128 mBar −10/+25 mBar at a temperature of 41° C.±3° C. for an aeration time of 1 hours −0/+12 hours, followed by external aeration for approximately 24 hours at 21° C.±3° C.

EXAMPLE 2

A lot of two balloon catheters were coated, post-processed, and sterilized with the same procedure as with Example 1. In this example, the fresh coating included 29% by weight paclitaxel and 71% by weight PEG-iodine excipient. Post-processing immersion was for 45 seconds at 70° F., at a 90 degree angle from horizontal, with no rotation. Drug density of paclitaxel (PTX) in µg/mm² was measured with high performance liquid chromatography (HPLC) for the fresh dry coating and the post-processed coating.

TABLE 3

|  | Fresh Dry Coating | 45 Seconds Post-Processing |
|---|---|---|
| PTX Loading (µg/mm²) | 2.13 | 2.00 |
| % PTX remaining from initial amount in dry fresh coating | — | 93.9 |

Table 3 provides the measured drug density in the coating for both a fresh coating and a coating post-processed for 45 seconds in accordance with an embodiment of the disclosure. In this embodiment, a withdrawal rate of 0.315 inches per second from the dip coating solution achieved a PTX loading of 2.13 µg/mm² in the dry fresh coating. As shown 0.13 µg/mm² of the paclitaxel was removed during the 45 second post-processing immersion to achieve a post-processed drug density of 2.00 µg/mm², which amounts to the coating retaining 93.9% of the original amount of paclitaxel from the fresh coating.

In accordance with embodiments of the disclosure, the processing sequence of Example 2 may be used to create a post-processed coating including 65-75 weight % paclitaxel and 25-35 weight % excipient in which greater than 75% of the original amount of excipient is removed from the coating during post-processing, while less than 10% of the paclitaxel is removed during post-processing

EXAMPLE 3

A lot of two balloon catheters were coated, post-processed, and sterilized with the same procedure as with Example 1. The only difference is that a different extraction speed from the coating solution was used in order to achieve a slightly higher loading of 2.25 µg/mm² on the balloon in the fresh coating, and post-processing immersion was for 5 minutes rather than 45 seconds in order to achieve a post-processed drug density of 2.00 µg/mm² on the balloon surface. Drug density of paclitaxel (PTX) in µg/mm² was measured with high performance liquid chromatography (HPLC) for the fresh dry coating and the post-processed coating.

TABLE 4

|  | Fresh Dry Coating | 5 Minutes Post-Processing |
|---|---|---|
| PTX Loading (µg/mm²) | 2.25 | 2.00 |
| % PTX remaining from initial amount in dry fresh coating | — | 88.9 |

Table 4 provides measured drug density in the coating for both a fresh coating and a coating post-processed for 5 minutes in accordance with an embodiment of the disclosure. In this embodiment, a withdrawal rate of greater than 0.315 inches per second from dip coating solution achieved a PTX loading of 2.25 μg/mm$^2$ in the dry fresh coating. As shown 0.25 μg/mm$^2$ of the paclitaxel was removed during the 5 minute post-processing immersion to achieve a post-processed drug density of 2.00 μg/mm$^2$, which amounts to the coating retaining 88.9% of the original amount of paclitaxel from the fresh coating.

In accordance with embodiments of the disclosure, the processing sequence of Example 3 may be used to create a post-processed coating including 80-85 weight % paclitaxel and 15-20 weight % excipient in which greater than 90% of the original amount of excipient is removed from the coating during post-processing, while less than 15% of the paclitaxel is removed during post-processing.

Comparing the results of Example 2 and Example 3, it has been demonstrated that varying the extraction speed from the dip coating solution can affect the resultant drug loading in the fresh coating. The results also demonstrate that increasing the post-processing immersion time can increase the amount of excipient selectively removed from the coating during post-processing between 45 seconds and 5 minutes. Both methods of Example 2 and Example 3 result in a post-processed coating including a drug loading of 2.00 μg/mm$^2$. However, as indicated in the corresponding discussions the process associated with Example 2 results in a post-processed coating composition with a higher weight % of excipient, and lower weight % paclitaxel compared to the process associated with Example 3.

As previously mentioned, a variety of systems can be produced in accordance with embodiments of the envision in which a therapeutic agent, excipient, and solvent system with a desired selectivity to the excipient are selected in order to accurately and reproducibly selectively remove the excipient and tune a desired amount of therapeutic agent on the medical device. In the particular embodiments in Examples 2 and 3, different processing conditions are demonstrated which both provide accurate and uniform drug densities of approximately 2.0 μg/mm$^2$. The drug density of approximately 2.0 μg/mm$^2$ has been selected in accordance with embodiments of the disclosure as a nominal value exhibiting clinical efficacy. However, embodiments are not limited, and other nominal values can be selected depending upon desired use.

EXAMPLE 4

A lot of balloon catheters were coated with the same procedure as with Example 1. The only difference is that the balloon catheters were ev3 EVERCROSS™, 4.0×40 mm. In process control UV spectroscopy results across nine balloon catheters from the lot indicated a fresh coating drug density of approximately 2.22 μg/mm$^2$±0.22 μg/mm$^2$ across the lot. The dried fresh coated balloons were then post-processed in four different groups described in Examples 4A-4D.

EXAMPLE 4A

A lot of 3 balloon catheters in accordance with Example 4 including dry fresh coatings were subjected to post-processing in a humidity chamber at 46° C. for one hour in order to provide a comparative baseline which is similar to the pre-conditioning stage of a three phase EtO sterilization process designed to provide conditions to incentivize micro organisms to come out of hibernation.

EXAMPLE 4B

A lot of 3 balloon catheters in accordance with Example 4 including dry fresh coatings were post-processed by immersion in 70° F. water for 5-10 seconds, with no rotation, and extracted at a rate of 1.2 inches per second.

EXAMPLE 4C

A lot of 3 balloon catheters in accordance with Example 4 including dry fresh coatings were post-processed by immersion in 70° F. water for 60 seconds, with no rotation, and extracted at a rate of 1.2 inches per second.

EXAMPLE 4D

A lot of 3 balloon catheters in accordance with Example 4 including dry fresh coatings were post-processed by immersion in 70° F. water for 300 seconds, with rotation at 60 RPM, and extracted at a rate of 1.2 inches per second.

Following post-processing, a lot of three balloon catheters for each group of balloon catheters in Examples 4A-4D was measured with gravimetric and UV spectroscopy analysis to quantify the weight % excipient on the post-processed balloon catheters. Weight % pactlitaxel was then calculated from the remaining percent of coating weight. Coating composition results for Examples 4A-4D are provided in the Table 5 below.

TABLE 5

| | Non-sterilized coating composition data. | | | | |
|---|---|---|---|---|---|
| | Fresh Dry Coating | (Example 1) Humidity | (Example 2) 5-10 Seconds Immersion | (Example 3) 60 Seconds Immersion | (Example 4) 300 Seconds Immersion |
| Weight % PTX | 29 | 30 | 52 | 81 | 86 |
| Weight % Excipient | 71 | 70 | 48 | 19 | 14 |

As shown in Table 5, post-processing in a humidity chamber at 46° C. for one hour did not change the composition of the coating. Alternatively, when the fresh coating is subjected to post-processing immersion in water significantly more excipient is removed from the coating than paclitaxel is removed from the coating, even for an immersion time as low as five to ten seconds. As shown, the selective removal of the excipient during post-processing causes the weight percent of the paclitaxel to increase in the post-processed coating. This can be attributed to the selective removal of the excipients to the paclitaxel which is at least 5 times, and may be more than 20 times, and even as high as 40 times.

A balloon catheter for each group was also subjected to a coating integrity test in which the post-processed coating was immersed in porcine serum, followed by inflation of the balloon to 12 atmospheres (atm), the inflated and immersed balloon was held in the porcine serum for 10 seconds, and then removed. Visual characteristics of the coating were observed while in porcine serum before inflation, while in porcine serum after inflation, and after removal from the procine serum. Observation of the coating integrity due to immersion in porcine serum was performed to provide an estimate for coating behavior in vivo. Following immersion in porcine serum, the coatings were removed from the balloon catheters and measured with UV spectroscopy quantify the amount of paclitaxel recovered after post-processing and immersion in porcine serum. Coating integrity results for Examples 4A-4D are provided in the Table 6 below.

5 and 300 seconds, followed by immersion in porcine serum or ten seconds. This suggests that post-processing the coating by water immersion to selectively remove a substantial portion of the excipient from the coating improves coating integrity, and consequently coating uniformity in vivo.

In an embodiment, the resultant post-processed coating retains a sufficient amount of a hydrophilic polymer or oligomer excipient so that the coating matrix is still capable of retaining the drug density within a hydrophilic medium which can aid in the transfer of a substantially water insoluble therapeutic agent such as paclitaxel across the boundary layer between the medical device coating and the adjacent body lumen tissue in vivo.

In an embodiment, a fresh coating composition is tailored to include one or more substantially water insoluble therapeutic agents such as paclitaxel and one or more excipients possessing chemical characteristics such that upon selection of the appropriate solvent system, the total excipient amount is selectively removed to obtain a post-processed coating

TABLE 6

Non-sterilized coating integrity data.

|  | Fresh Dry Coating | (Example 1) Humidity | (Example 2) 5 Seconds Immersion | (Example 3) 60 Seconds Immersion | (Example 4) 300 Seconds Immersion |
|---|---|---|---|---|---|
| Coating characteristics immersion in porcine serum before inflation | Clear, yellow, no flaking | Clear, some flakes | Clear, yellow, no flaking | White, opaque, no flaking | White, opaque, no flaking |
| Coating characteristics immersion in porcine serum after inflation | — | Significant flaking | No flaking | No flaking | No flaking |
| Coating characteristics after removal from porcine serum | — | Significant flaking | No flaking | No flaking | No flaking |
| PTX Loading ($\mu g/mm^2$) | 2.22 | 1.64 | 2.13 | 2.00 | 2.10 |
| % PTX recovered from initial amount | — | 73.9 | 96.1 | 89.9 | 94.5 |

As shown in Table 5, post-processing in a humidity chamber at 46° C. for one hour did not change the composition of the coating, which was measured at 70 wt % excipient, and 30 wt % pactlitaxel. However, as shown in Table 6, flaking was observed during immersion in porcine serum, and after immersion in porcine serum. It is believed that the flaking of the coating during immersion in porcine serum is attributed to the coating absorbing moisture in the humidity chamber.

It is also believed that the flaking of the coating during immersion in porcine serum strongly contributed to recovering only 73.9% of the paclitaxel from the initial amount of paclitaxel which was originally contained in the dry fresh coating.

Still referring to Table 6, the coating integrity tests for Examples 2-4 corresponding to post-processing immersion from 5 to 300 seconds demonstrate improved coating integrity during and after immersion in porcine serum with no flaking compared to Example 1. Furthermore, greater than 85%, and even more than 90%, of the initial amount of pacltitaxel originally contained in the dry fresh coating was recovered from Examples 2-4 after post-processing between including a drug density required to provide clinical efficacy and suitable mechanical characteristics so that functionality of the coating is not lost during clinical use. In accordance with embodiments of the disclosure, a coating process including post-processing and sterilization has been demonstrated that repeatedly produces coatings with good mechanical properties with little to no flaking, and with good coating uniformity across the device surface at accurate drug densities of 0.1-10 $\mu g/mm^2 \pm 10\%$ nominal value, or more specifically 0.7-3.0 $\mu g/mm^2 \pm 10\%$ nominal value. In an embodiment, the resultant post-processed and sterilized coating has a drug density of approximately 2.0 $\mu g/mm^2 \pm 0.2$ $\mu g/mm^2$.

EXAMPLE 5

Figure 7:
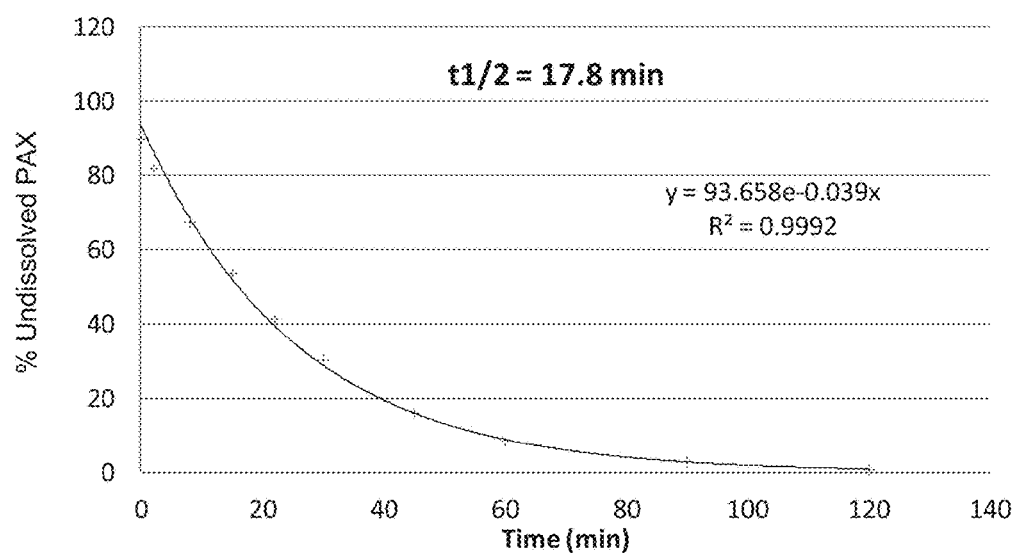
FIG. 7 is dissolution profile for the amount of undissolved paclitaxel in shaker baths of 50/50 methanol/water at 37° C. as a function of time in accordance with an embodiment of the disclosure.

Ten balloon catheters were coated, post-processed, and sterilized with the same procedure as with Example 1. The balloons were then separately immersed in separate shaker baths of 50/50 methanol/water (MeOH/H$_2$O) at 37° C. at different time intervals between 0 and 120 minutes. Each balloon was then tested for paclitaxel amount with an ultraviolet spectrophotometer. The dissolution profile for the amount of undissolved paclitaxel as a function of time is provided in FIG. 7.

EXAMPLE 6

Figure 8:
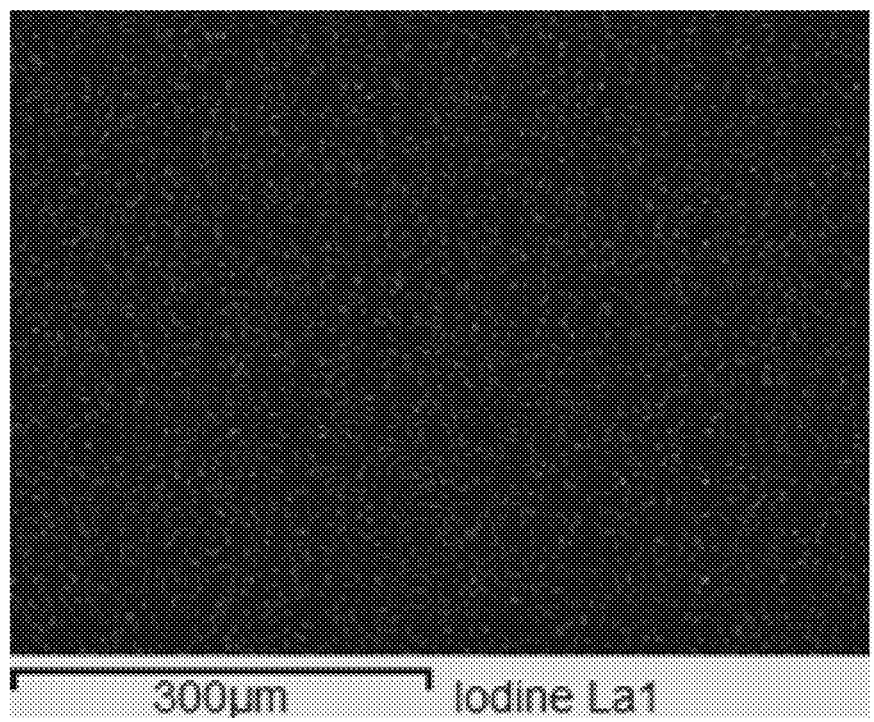
FIG. 8 is an SEM EDX image illustrating iodine content in accordance with an embodiment of the disclosure.

A balloon catheter was coated, post-processed, and sterilized with the same procedure as with Example 1. The coating surface was then inspected with SEM EDX for iodine content. The SEM EDX image is provided in FIG. 8 in which the iodine is represented by the white specs, or portions of the image. As shown, the iodine is uniformly dispersed in the coating.

EXAMPLE 7

Figure 9:
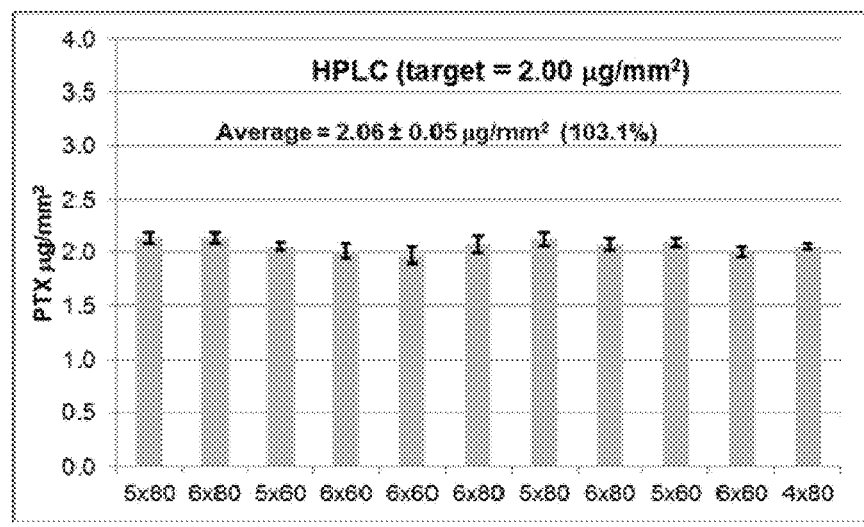
FIG. 9 illustrates drug density for different balloon sizes in accordance with an embodiment of the disclosure.

Eleven balloon catheter lots of different diameter and working length were coated, post-processed, and sterilized with the same procedure as with Example 1. Each balloon lot included 10 balloon catheters. Balloon sizes included in mm diameter by mm working length: 5×80, 6×80, 5×60, 6×60, 6×80, 4×80 mm. The results provided in FIG. 9 illustrate consistent drug density for the different balloon sizes. Each balloon was tested for paclitaxel amount with HPLC. Average drug density was determined to be 2.06±0.05 µg/mm$^2$, which corresponds to 103.1% of a target 2.00 µg/mm$^2$.

Figure 10:
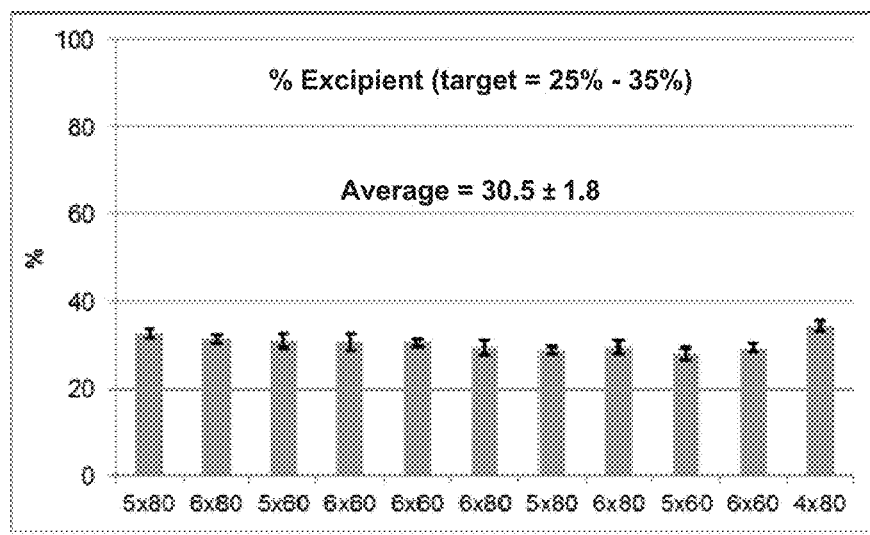
FIG. 10 illustrates excipient weight percent for different balloon sizes in accordance with an embodiment of the disclosure.

Based upon the HPLC results in FIG. 9, the % PEG-iodine excipient was calculated with gravimetric analysis in combination with the HPLC results. The results provided in FIG. 10 illustrate consistent percentages of PEG-iodine excipient for the different balloon sizes. Average weight percent PEG-iodine excipient was determined to be 30.5%±1.8%, for a target weight percent of 30%±5%. The error bar for each lot in both FIG. 9 and FIG. 10 illustrates a single standard deviation for the specific lot.

Figure 11:
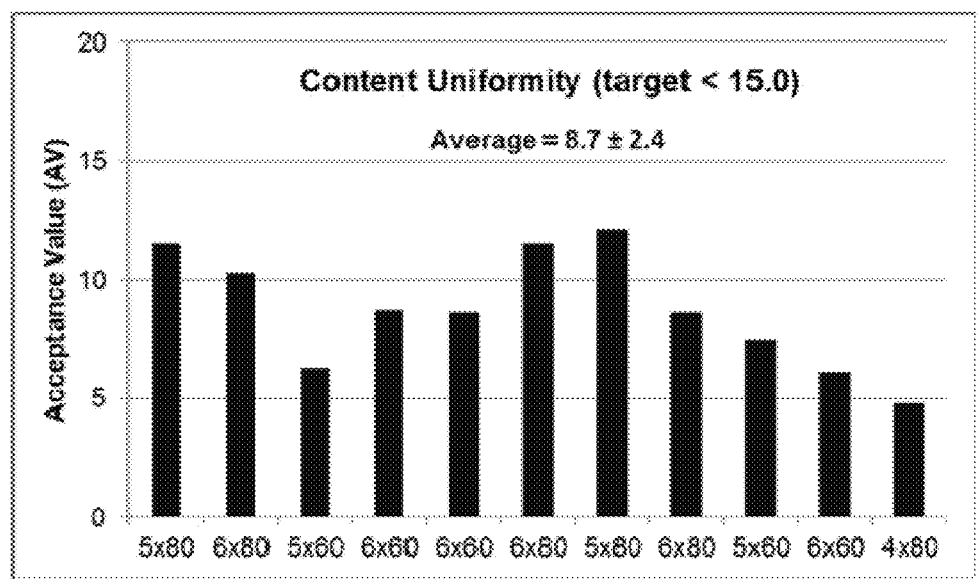
FIG. 11 illustrates Acceptance Values (AV) for Content Uniformity in accordance with USP <905> for different balloon sizes in accordance with an embodiment of the disclosure.

Referring now to FIG. 11, the Acceptance Value (AV) was calculated for each lot of devices in accordance with the United States Pharmacopeia's (USP) chapter 905, "Uniformity of Dosage Units." In these tests an AV of less than 15 is indicative of a device lot whose coating is uniform throughout the lot. As illustrated in FIG. 11, each device lot had an AV of less than 15, with an average AV across the eleven device lots of 8.7±2.4.

EXAMPLE 8

Three lots of ten balloon catheters were coated and sterilized with the same procedure as with Example 1, except the balloons were not post-processed. Visually, the coating on the balloon catheters after sterilization for each lot appeared flaky and was easily removed from the balloon surface. Total drug (pactilaxel) content before (TDC-B) was measured for each device lot prior to sterilization, and Total drug (paclitaxel) content (TDC-A) and Acceptance Value (AV) was measured for each device lot after sterilization. The results are provided in Table 7. The drop in paclitaxel amount from TDC-B to TDC-A is due to mechanical loss attributed to poor coating integrity. The high Acceptance Values (>15.0=Fail) reflects the randomness of the loss of coating material.

TABLE 7

| Balloon Catheter Lot | Balloon Size (mm) | TDC-B (µg/mm$^2$) | TDC-A (µg/mm$^2$) | AV |
|---|---|---|---|---|
| 1 | 3 × 20 | 2.25 ± 0.10 | 1.71 ± 0.20 | 37.2 |
| 2 | 6 × 40 | 2.22 ± 0.08 | 1.82 ± 0.10 | 18.9 |
| 3 | 7 × 80 | 2.22 ± 0.06 | 1.88 ± 0.07 | 13.1 |

EXAMPLE 9

Fifteen lots of ten balloon catheters were coated, post-processed, and sterilized with the same procedure as with Example 1. Total drug (pactilaxel) content before (TDC-B) was measured for each device lot prior to sterilization. Total drug (paclitaxel) content (TDC-A) and Acceptance Value (AV) was measured for each lot after sterilization. In addition percent coating loss (CL) was measured as the percent coating dislodged upon dry expansion of a post-sterilization dry balloon to nominal inflation pressure. The results are provided in Table 8. The drop in paclitaxel amount from TDC-B to TDC-A is not due to mechanical loss attributed to poor coating integrity. Instead the drop is attributed to the partial dissolution of paclitaxel in the post-processing water immersion operation, which may be aided by the presence of iodine in the coating.

TABLE 8

| Balloon Catheter Lot | Balloon Size (mm) | TDC-B (µg/mm$^2$) | TDC-A (µg/mm$^2$) | AV | CL (%) |
|---|---|---|---|---|---|
| 4 | 5 × 80 | 2.21 ± 0.06 | 2.13 ± 0.05 | 11.5 | 0.6 |
| 5 | 6 × 80 | 2.24 ± 0.04 | 2.13 ± 0.05 | 10.3 | 0.4 |
| 6 | 5 × 60 | 2.21 ± 0.06 | 2.05 ± 0.04 | 6.3 | 1.0 |
| 7 | 6 × 60 | 2.18 ± 0.06 | 2.01 ± 0.07 | 8.7 | 0.5 |
| 8 | 6 × 60 | 2.13 ± 0.05 | 1.97 ± 0.07 | 8.6 | 0.5 |
| 9 | 6 × 80 | 2.24 ± 0.10 | 2.07 ± 0.08 | 11.5 | 1.2 |
| 10 | 5 × 80 | 2.21 ± 0.06 | 2.12 ± 0.06 | 12.1 | 1.7 |
| 11 | 6 × 80 | 2.14 ± 0.06 | 2.07 ± 0.06 | 8.6 | 1.0 |
| 12 | 5 × 60 | 2.25 ± 0.07 | 2.09 ± 0.04 | 7.5 | 0.2 |
| 13 | 6 × 60 | 2.11 ± 0.05 | 2.00 ± 0.05 | 6.1 | 0.2 |
| 14 | 4 × 80 | 2.16 ± 0.06 | 2.05 ± 0.03 | 4.8 | 1.0 |
| 15 | 5 × 40 | 2.25 ± 0.08 | 2.16 ± 0.05 | 12.3 | 0.7 |
| 16 | 6 × 40 | 2.13 ± 0.06 | 2.00 ± 0.09 | 11.2 | 0.6 |
| 17 | 5 × 40 | 2.11 ± 0.04 | 2.03 ± 0.06 | 7.8 | 0.1 |
| 18 | 6 × 40 | 2.14 ± 0.09 | 1.99 ± 0.06 | 7.6 | 0.2 |

Furthermore, the coatings for balloon catheter lots 4-18 did not readily flake off of the balloon surfaces, which demonstrates that the post-processing produces a controlled morphology with superior mechanical properties resulting in reduced ductile failure as evidenced by the percent coating loss tests. The results of Table 7 and Table 8 indicate that by performing post-processing in accordance with embodiments of the disclosure one can tune in on a high drug doses of 0.1-10 µg/mm$^2$, or more specifically 0.7-3.0 µg/mm$^2$, required for clinical efficacy within ±10% nominal value (e.g. 2.00±0.2 µg/mm$^2$) while still meeting the stringent Acceptance Value of USP chapter 905, which may not be possible without post-processing.

In the foregoing specification, various embodiments of the disclosure have been described for post-processing of a coated medical device, and specifically a coated balloon of a balloon catheter. The coatings may also be applied to one or more surfaces of other medical devices adapted for temporary or permanent placement in the body. For example, such medical device may include, but are not limited to, stents, stent grafts, vascular grafts, catheters, flexible or rigid endoscopes, flexible or rigid bronchoscopes, guide wires, balloons, filters (e.g. vena cava filters), cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves (e.g. venous valves), abdominal aortic aneurysm (AAA) grafts, embolic coils, various types of dressings, bone substitutes, intraluminal devices, vascular supports, or other known bio-compatible devices.

Figure 12A:
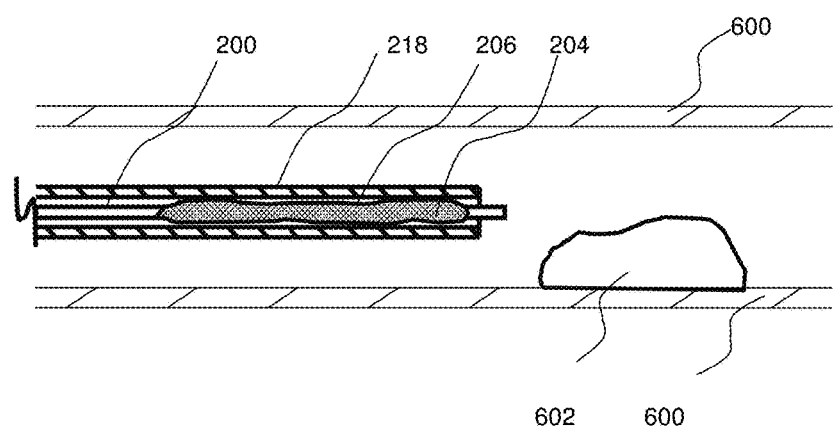
FIG. 12A is a cross-sectional side view illustration of an unexpanded balloon of a balloon catheter covered by a retractable sheath and inserted into a body lumen in accordance with an embodiment of the disclosure.
Figure 12B:
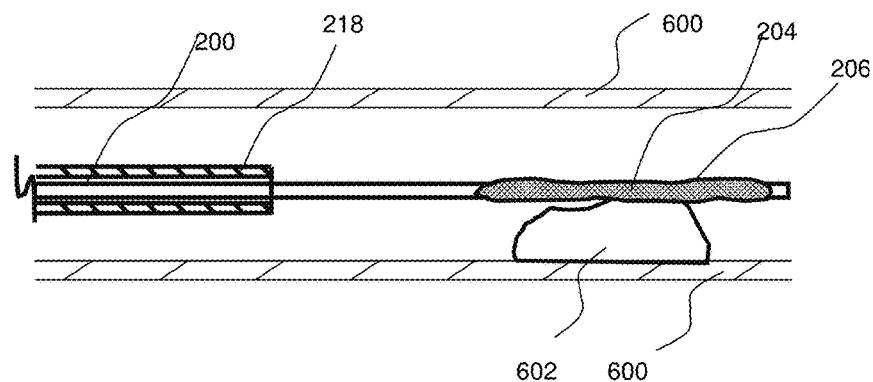
FIG. 12B is a cross-sectional side view illustration of an unexpanded balloon of a balloon catheter adjacent a focal area of local therapeutic agent delivery within a body lumen in accordance with an embodiment of the disclosure.
Figure 12C:
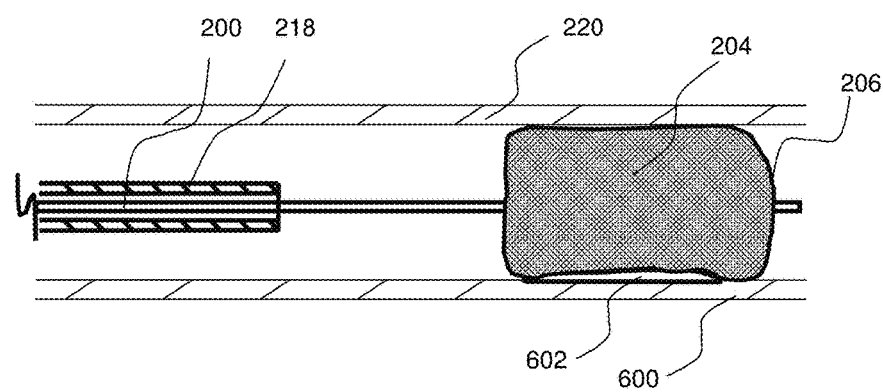
FIG. 12C is a cross-sectional side view illustration of an expanded balloon of a balloon catheter at a focal area of local therapeutic agent delivery within a body lumen in accordance with an embodiment of the disclosure.

FIGS. 12A-FIG. 12C are illustrations of a particular embodiment in which the therapeutic agent is locally delivered to the surface of a body lumen. As shown in FIG. 12A a post-processed and sterilized balloon catheter 200 having a coating 206 disposed on an unexpanded balloon 204 is provided and inserted into a body lumen 600. The catheter 200 may additionally include an optional protective sheath 218 over the unexpanded balloon 204 to prevent the coating 206 from prematurely dissolving when the catheter is inserted into the body lumen 600. In an embodiment, the body lumen 600 may be an artery including a focal area 602, such as an unperturbed primary atheroscolerotic or restenotic lesion. In an embodiment, the body lumen 600 may be a common bile duct or a branch of a common bile duct and focal area 602 is an intraluminal tumor.

As shown in FIG. 12B, the unexpanded balloon 204 is positioned adjacent the focal area 602 and the protective sheath 218 is retracted. As shown in FIG. 12C, the balloon 204 is then expanded (by inflation or otherwise) to contact the coating 206 on the expanded balloon 204 against the body lumen 600 where the focal area 602 exists. In an embodiment, the expanded balloon 204 is a balloon catheter and the balloon is expanded to 2-20 atmospheres. Possessing a hydrophilic character, the coating 206 dissolves when exposed to aqueous fluids such as blood in vivo.

In clinical use for angioplasty, it may be preferable for the balloon 204 to be expanded for only 5 to 300 seconds in a touch and go procedure. This time limitation is due to the type of medical procedure because a longer use time with the balloon inflated could result in focal or adjacent tissue damage that is deleterious to the therapeutic intent of the procedure. This damage could result from mechanical pressure and/or metabolic insufficiency caused by sustained inflation of the balloon including but not limited to tissue architecture, tissue inflammation, cell death, and induction of reactive scarring within the organ. In an embodiment, a coated angioplasty balloon may be tracked to a target lesion using standard techniques, the optional protective sheath is retracted and the angioplasty balloon is inflated against an artery wall. Hydration of the coating occurs immediately and causes the therapeutic agent to release into tissue, the coating polymer or oligomer to dissolve, and some of the coating to transfer from the balloon to the artery wall. This paving acts as drug reservoir and is transient. The significant or total solubility of the polymer or oligomer in blood prevents embolic hazards associated with the coating. Also, this active dissolution of the polymer or oligomer matrix assists the transfer of hydrophobic and substantially water-insoluble therapeutic agents such as paclitaxel from the balloon to the tissue.

Diseases of the Vasculature

One therapeutic area where embodiments of the present disclosure will be applicable is the treatment of luminal disorders of the vasculature. In general, luminal disorders may be classified as native (atherosclerotic, thromboembolic) or iatrogenic (restenosis) diseases. These luminal disorders may include but not be limited to atherosclerosis, atheromatous lesions, vulnerable plaque, thromboembolic obstructions, vascular graft disease, arteriovenous fistula disease, arteriovenous graft disease and restenosis.

Atherosclerosis is a complex disease of the vessel wall involving the interplay of inflammation, proliferation, lipid deposition and thrombus formation. Atherosclerosis promotes the formation of atheromatous plaques that may progress slowly over several years, leading to progressive obstruction of the vessel lumen manifesting clinically as angina. Atheromatous plaques, may also become "vulnerable plaques" due to an unstable collection of white blood cells (primarily macrophages) and lipids (including cholesterol) in the wall of an artery and become particularly prone to rupture. A rupture of a vulnerable plaque is commonly believed to be the cause of sudden thrombotic obstructions of the vessel lumen due to the rapid formation of blood clots at the rupture site, leading to the clinical manifestations of heart attack or stroke. Vulnerable plaques may not significantly obstruct a vessel lumen until rupture, thus they are pre-obstructive lesions. It is envisioned that a desirable therapeutic target is the prevention of obstruction of the vessel lumen by the treatment of vulnerable plaques prior to their rupture. Specifically, embodiments of the present disclosure could be applied to a catheter with a tip that is expandable to allow uniform and complete contact with and delivery of therapeutic agents to sites of luminal atheromatous or vulnerable plaques. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy.

Restenosis

One therapeutic area where embodiments of the present disclosure will be applicable is inhibiting the process of restenosis. Restenosis is the result of a complex process involving inflammation and proliferation activated by a response to a percutaneous or surgical vascular intervention. Examples of these percutaneous or surgical interventions may include but are not limited to the revascularization of vascular bypass grafts, arteriovenous fistulas, arteriovenous grafts and percutaneous revascularization of coronary, femoral, and carotid vessels. Atherosclerotic plaque arising from the arterial wall can reduce cross-sectional flow area which limits flow to downstream organs. Cross-sectional flow area can be restored by displacing (e.g. expandable balloon or stent) or removing the lesion (e.g. directional or rotational atherectomy). In the months to weeks after revascularization local proliferative of arterial wall smooth muscle cells can create an obstruction to flow at the site of the original atherosclerotic plaque. Paclitaxel is a diterpene molecule containing a complex taxane ring that inhibits cytokinesis by promoting microtubule polymerization. Paclitaxel inhibits smooth muscle cell proliferation and restenosis after balloon angioplasty in a mammalian arteries. Paclitaxel inhibits restenosis after percutaneous coronary revascularization in humans when it is delivered over days to weeks from implanted metal stents that were retained after the revascularization procedure. Brief exposure to paclitaxel (20 minutes of less) can inhibit smooth muscle cell proliferation for sustained periods (14 days). Clinical studies demonstrate that paclitaxel can also effectively inhibit restenosis after femoral and coronary revascularization when it is delivered over a short period (minutes) from an expandable balloon coated with the drug.

Restenosis is a complex molecular process that involves both smooth muscle cell proliferation in addition to inflammatory processes. Dexamethasone is a glucocorticoid that reduces inflammation and restenosis after balloon angioplasty in a mammalian arteries. This suggests that there may be clinical benefit in delivering antimitotic agents such as paclitaxel in combination with anti-inflammatory agents such as dexamethasone from an expandable balloon coated with the two therapeutic agents.

Pulmonary Disease

Another therapeutic area where embodiments of the present disclosure could be applicable is a luminal surface of normal or diseased airway for the treatment or prevention of focal diseases of the lung and airways. This embodiment may be used in conjunction with both a rigid or flexible bronchoscope which are commonly used to facilitate access to and visualization of the target treatment area.

In general, focal diseases of the airways area neoplasms that are categorized as either benign or malignant. Primary neoplasms may be classified as epithelial, mesenchymal or lymphoid tumors; more than 20 types of tracheal neoplasms have been described.

Carcinoid tumors represent approximately 85 percent of adenomas of the tracheobronchial tree. Adenoid cystic carcinoma is the most frequent adenoma of the trachea. Adenoid cystic carcinoma (or cylindroma) is the second most common malignancy and also the second most common primary tracheal neoplasm.

Conventional treatment for lung cancer can involve surgical removal of tumor, chemotherapy, or radiation therapy, as well as combinations of these methods. The decision about which treatments will be appropriate take into account the localization and extent of the tumor as well as the overall health status of the patient. An example of adjuvant therapy is chemotherapy or radiotherapy administered after surgical removal of a tumor in order to be certain that all tumor cells are killed.

Depending upon the specific neoplasm type and behavior as well as the time of diagnosis, the neoplasm may or may not present a physical obstruction or protrusion into the lumen of the airways. It is envisioned that an approach to restoring functional luminal patency could be to mechanically restore luminal patency by displacing the tumor with a balloon or reduce tumor bulk and then locally delivering a drug to inhibit tumor growth and/or tumor survival. Local drug delivery using embodiments of the present disclosure could be an effective method of delivering chemotherapeutic agents effective against benign or malignant neoplasms to the luminal aspect of the tumor. Specifically, embodiments of the present disclosure could be applied to a catheter or a bronchoscope and advanced antegradely or retrogradely to the intended site of local drug delivery. It is envisioned that embodiments of the present disclosure will enable the local delivery of bioactive (therapeutic) agents to the surface of normal or diseased airway lumens and may be used singly or in combination with surgical removal, chemotherapy and radiation therapy. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy. The targeted local delivery of therapeutic agents may be used to reduce tumor size to facilitate surgical removal and may eliminate the need for and/or reduce the duration or intensity of systemic chemotherapy or radiotherapy which have numerous unpleasant side effects.

Gastrointestinal Disease

Another therapeutic area where embodiments of the present disclosure could be applicable is gastrointestinal disease including, but limited to, benign and malignant tumors of the esophagus, biliary tract, colon, and small bowel.

Esophageal tumors are caused by dysregulated division of esophageal smooth muscle or epithelial cells. The tumors can be either benign (e.g. leiomyoma) or malignant (squamous cell carcinoma or adenocarcinoma). These tumors can grow into the lumen and compromise the functional cross-sectional area of the esophagus causing dysphagia (abnormal swallowing) and consequent malnutrition.

It is envisioned that an approach to restoring functional luminal patency could be to mechanically restore luminal patency by displacing the tumor with a balloon or metal dilator or reduce tumor bulk (e.g. laser ablation), and then locally delivering a therapeutic agent to inhibit tumor growth and/or tumor survival. Local therapeutic agent delivery using embodiments of the present disclosure could be an effective method of delivering chemotherapeutic agents effective against benign or malignant esophageal tumors to the luminal aspect of the tumor. Specifically, embodiments of the present disclosure could be applied to a catheter or an endoscope and advanced antegradely or retrogradely to the intended site of local drug delivery. Chemotherapeutic agents that could be effective in this manner include, but are not limited to, microtubule stabilizing agents (e.g. taxanes including paclitaxel and epothilones), topoisomerase I inhibitors (e.g. irinotecan), platinum derivatives (e.g. oxaliplatin, cisplatin, carboplatin), anthracyclines (daunorubicin, epirubicin), 5-FU, and targeted biologic therapies (e.g. anti-VEGF antibodies such as bevacizumab). The advantages of this method are that high doses of effective chemotherapeutic agents can be delivered to the tumor without systemic toxicity, the patient's diet would not have to be modified to prevent food impaction, and the mechanical complications of stent placement including indirect tracheal compression, stent migration, and stent occlusion could be avoided. Therapeutic agent for the above indication that exhibit water-only solubility or require water for solubilization such as carboplatin, cisplatin, the epothilones, and targeted proteins such as antibodies (such as the anti-VEGF antibody bevacizumab) can be formulated into the disclosed coating by the use of water as part or all of the solvent.

A similar approach could be used with malignancies of the biliary tract. Cholangiocarcinoma is the most common biliary tract malignancy. It is caused by dysregulated division of cholangiocytes. These tumors can compromise the functional lumen of the intra- or extra-hepatic biliary tree causing cholestasis and consequent cholangitis, pruritis, fat malabsorption, and anorexia.

It is envisioned that an approach to restoring functional luminal patency could be to mechanically restore luminal patency by displacing the tumor with a balloon, blade, or metal dilator or reduce tumor bulk (e.g. laser ablation), and then locally deliver a therapeutic agent to inhibit tumor growth and/or tumor survival utilizing embodiment of the present disclosure. Chemotherapeutic agents that could be effective in this manner include, but are not limited to, microtubule stabilizing agents (e.g. taxanes including paclitaxel and epothilones), platinum derivatives (e.g. oxaliplatin, cisplatin, carboplatin), anthracyclines (daunorubicin, epirubicin), 5-FU, DNA cross-linkers (mitomycin-C), alkylating nitrosoureas (lomustine), interferons (interferon-alpha), and targeted biologically active agents (e.g. EGFR inhibitors such as cetuximax). The advantages of this method are that high doses of effective chemotherapeutic agents can be delivered to the tumor without systemic toxicity, and the mechanical complications of stent placement including stent migration and stent occlusion could be avoided.

Approaches similar to that described above for esophageal and biliary tract malignancies could be developed for small bowel and colonic malignancies. Analogous approaches could also be used to locally delivery therapeutic agents to non-malignant gastrointestinal diseases (e.g. anti-inflammatory agents delivered to treat inflammatory bowel disease). Therapeutic agents for the above indication that exhibit water-only solubility or require water for solubilization such as carboplatin, cisplatin, the epothilones, interferons (interferon-alpha) and targeted proteins such as antibodies (such as the EGFR inhibitor cetuximab) can be formulated into the disclosed coating by the use of water as part or all of the solvent system.

In the foregoing specification, various embodiments of the disclosure have been described. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method of forming a coated medical device comprising:
    applying a coating to an outer surface of a medical device by dip coating the medical device into a solution including a therapeutic agent dispersed in a matrix of a polymer or oligomer excipient while rotating the medical device;
    post-processing the medical device by immersion in a solvent or solution, thereby selectively removing a substantial portion of the polymer or oligomer excipient from the matrix in which the therapeutic agent is dispersed; and
    sterilizing the post-processed medical device,
    wherein the coating comprises less than 50% by weight of the therapeutic agent prior to post-processing, and the coating comprises greater than 50% by weight of the therapeutic agent after post-processing.

2. The method of claim 1, wherein dip coating the medical device into the solution occurs at an angle from 45 degrees to 90 degrees from horizontal.

3. The method of claim 1, wherein rotating the medical device occurs at a rate from 10 to 100 revolutions per minute.

4. The method of claim 1, wherein the coating comprises 35% or less by weight of the therapeutic agent prior to post-processing, and the coating comprises 65% or more by weight: of the therapeutic agent after post-processing.

5. The method of claim 1, wherein less than 10% by weight of the therapeutic agent is removed from the coating during post-processing.

6. The method of claim 5, wherein greater than 75% by weight of the polymer or oligomer excipient is removed from the coating during post-processing.

7. The method of claim 1, wherein less than 15% by weight of therapeutic agent is removed from the coating during post-processing.

8. The method of claim 7, wherein greater than 90% of the polymer or oligomer excipient is removed from the coating during post-processing.

9. The method of claim 1, wherein the wherein the therapeutic agent includes a taxane.

10. The method of claim 9, wherein the taxane is selected from the group consisting of paclitaxel, paclitaxel analogues, and paclitaxel derivatives thereof.

11. The method of claim 1, wherein the solution includes:
    paclitaxel;
    iodine;
    a polymer; and
    a solvent.

12. The method of claim 11, wherein the polymer is soluble in both water and a solvent solution comprising an organic solvent and less than 20% by weight water.

13. The method of claim 11, wherein the polymer has a molecular weight below 20,000 Daltons.

14. The method of claim 13, wherein the polymer is polyethylene glycol (PEG).

15. The method of claim 11, wherein the solvent includes a mixture of ethanol and acetonitrile.

16. The method of claim 1, wherein post-processing the medical device comprises immersing the medical device in an aqueous solution.

17. The method of claim 16, wherein immersing the medical device in the aqueous solution comprises immersing the medical device in the aqueous solution for 5 minutes or less.

18. The method of claim 1, wherein post-processing the medical device comprises immersing the medical device in a solution comprising an organic solvent, optionally in combination with water.

19. The method of claim 1, wherein sterilizing the post-processed medical device comprises exposing the medical device to a relative humidity.

20. The method of claim 1, wherein sterilizing comprises a pre-conditioning stage, a sterilization stage, and an aeration stage.

* * * * *